(12) United States Patent
Chatzizisis

(10) Patent No.: US 12,096,986 B2
(45) Date of Patent: *Sep. 24, 2024

(54) COMPUTATIONAL SIMULATION PLATFORM FOR PLANNING OF INTERVENTIONAL PROCEDURES

(71) Applicant: The Board of Regents of the University of Nebraska, Lincoln, NE (US)

(72) Inventor: Ioannis S. Chatzizisis, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 605 days.

This patent is subject to a terminal disclaimer.

(21) Appl. No.: 17/314,338

(22) Filed: May 7, 2021

(65) Prior Publication Data

US 2021/0259777 A1 Aug. 26, 2021

Related U.S. Application Data

(63) Continuation-in-part of application No. 17/076,213, filed on Oct. 21, 2020, now Pat. No. 11,026,749.
(Continued)

(51) Int. Cl.
*A61B 34/10* (2016.01)
*A61B 90/00* (2016.01)
*G06T 17/20* (2006.01)

(52) U.S. Cl.
CPC .............. *A61B 34/10* (2016.02); *A61B 90/37* (2016.02); *G06T 17/20* (2013.01);
(Continued)

(58) Field of Classification Search
CPC ... A61B 34/10; A61B 90/37; A61B 2034/102; A61B 2034/105; A61B 2090/3762;
(Continued)

(56) References Cited

U.S. PATENT DOCUMENTS 6,381,350 B1 4/2002 Klingensmith
10,140,733 B1 11/2018 Liu et al.
(Continued)

FOREIGN PATENT DOCUMENTS

DE 102007039207 A1 2/2009
WO 2018108640 A1 6/2018

OTHER PUBLICATIONS

International Search Report and Written Opinion for PCT/US2020/057304 mailed Jan. 27, 2021.
(Continued)

*Primary Examiner* — Ping Y Hsieh
*Assistant Examiner* — Jose M Torres
(74) *Attorney, Agent, or Firm* — Foley Hoag LLP; Erik Huestis; Lee Chedister

(57) ABSTRACT

In accordance with embodiments of this disclosure, a computational simulation platform comprises a computer-implemented method that includes: generating a mesh or meshless three-dimensional (3D) reconstruction of a vessel lumen and a surface of the vessel lumen based on invasive or non-invasive imaging; assigning material properties to the 3D reconstructed surface of the vessel lumen based on the invasive or non-invasive imaging; performing balloon pre-dilation, stenting and balloon post-dilation computational simulations with the 3D reconstructed vessel lumen and surface of the vessel lumen; and assessing stent and vessel morphometric and biomechanical measures based on the computational simulations.

20 Claims, 16 Drawing Sheets

Related U.S. Application Data

(60) Provisional application No. 62/944,054, filed on Dec. 5, 2019.

(52) U.S. Cl.
CPC ... *A61B 2034/102* (2016.02); *A61B 2034/105* (2016.02); *A61B 2090/3762* (2016.02); *A61B 2090/378* (2016.02); *G06T 2210/41* (2013.01)

(58) Field of Classification Search
CPC ... A61B 2090/378; A61B 34/01; G06T 17/20; G06T 2210/41; G16H 30/40; G16H 50/50
See application file for complete search history.

(56) References Cited

U.S. PATENT DOCUMENTS

| | | |
|---|---|---|
| 11,026,749 B1 | 6/2021 | Chatzizisis |
| 2003/0195411 A1 | 10/2003 | Sureda et al. |
| 2005/0107688 A1 | 5/2005 | Strommer |
| 2006/0127867 A1 | 6/2006 | Grund-Pedersen |
| 2008/0286735 A1 | 11/2008 | Cusano |
| 2009/0304245 A1 | 12/2009 | Egger et al. |
| 2012/0053466 A1 | 3/2012 | Bianchi et al. |
| 2012/0084064 A1 | 4/2012 | Dzenis et al. |
| 2013/0064343 A1 | 3/2013 | Verstraelen et al. |
| 2013/0132054 A1 | 5/2013 | Sharma et al. |
| 2015/0112659 A1 | 4/2015 | Mortier |
| 2016/0206208 A1* | 7/2016 | Yamamoto ........... A61B 5/7257 |
| 2017/0018116 A1 | 1/2017 | Sun et al. |
| 2020/0237329 A1 | 7/2020 | Min |
| 2020/0352536 A1 | 11/2020 | Samady et al. |

OTHER PUBLICATIONS

Xu et al., "Mechanical response of cardiovascular slants under vascular dynamic bending", BioMedical Engineering Online (2016) 15:21, pp. 1-20 (Year: 2016).
Jie et al., "Simulation of Stent Expansion by Finite Element Method", 2009 3rd International Conference on Bioinformatics and Biomedical Engineering, pp. 1-4 (Year: 2009).
Gijsen et al., "Simulation of stent deployment in a realistic human coronary artery", Biomedical Engineering Online, Biomed Central Ltd, London, GB, vol. 7, No. 1, Aug. 6, 2008 (Aug. 6, 2008), p. 23.
Supplementary Partial European Search Report for EP Application No. 20897527.6 dated Mar. 20, 2024.

* cited by examiner

COMPUTATIONAL SIMULATION PLATFORM FOR PLANNING OF INTERVENTIONAL PROCEDURES

CROSS-REFERENCE TO RELATED APPLICATIONS

The present application is a continuation-in-part of U.S. Nonprovisional patent application Ser. No. 17/076,213, filed Oct. 21, 2020, and titled "COMPUTATIONAL SIMULATION PLATFORM FOR PLANNING OF INTERVENTIONAL PROCEDURES," which claims the benefit under 35 U.S.C. § 119(e) of U.S. Provisional Application Ser. No. 62/944,054, filed Dec. 5, 2019, and titled "COMPUTATIONAL SIMULATION PLATFORM FOR PLANNING OF INTERVENTIONAL PROCEDURES," which is incorporated herein by reference in its entirety.

STATEMENT OF GOVERNMENT SUPPORT

This invention was made with U.S. government support under grant number R01 HL144690 awarded by the National Institutes of Health (NIH). The U.S. government has certain rights in the invention.

TECHNICAL FIELD

The present invention generally relates to systems and methods for simulating and planning interventional procedures.

BACKGROUND

Coronary artery disease is the leading cause of death in Western society. Stents are implanted in 70-90% of the 1.3 million percutaneous coronary interventions performed annually in the US, of which 20% involve bifurcations. Coronary bifurcations remain one of the most challenging lesion subsets in interventional cardiology, with a lower procedural success rate and increased rates of adverse cardiac events, ranging between 15-20% at 6 months to 1 year post-intervention. In lieu of the continuously increasing frequency of complex coronary interventions (including bifurcations), the incidence of bifurcation-related adverse outcomes is anticipated to further increase. Even though drug-eluting stents attenuate neointimal formation, restenosis with drug-eluting stents is still significant, particularly in bifurcation lesions compared to unbranched segments, suggesting that the stenting technique and the associated biomechanical environment play a dominant role in the restenosis propensity of this anatomical subset. Indeed, drug-eluting stents do not address the fundamental fluid and solid mechanics associated with stents, which appear to significantly contribute to stent restenosis, especially in bifurcations. Despite the great interest in coronary bifurcations and the multiple proposed technical strategies, percutaneous intervention of bifurcations remains challenging, and the ideal treatment strategy is still elusive.

Since no two bifurcations are identical, no single treatment strategy exists that can be applied to every bifurcation. The most important issue in bifurcation interventions is selecting the most appropriate technique tailored to a specific bifurcation. Computational simulations have the potential to assess the local hemodynamic microenvironment in bifurcations pre- and post-stenting, providing important insights into the role of local biomechanical stresses on neointimal hyperplasia and stent thrombosis. The quantitative association of post-intervention hemodynamics with anatomical stent restenosis can help optimize stenting techniques and stent design, ultimately improving clinical outcomes. In the modern era of robust computations, bifurcation stenting simulations using patient-specific anatomy and high-resolution intracoronary imaging modalities (e.g., optical coherence tomography, intravascular ultrasound), as well as realistic boundary conditions and materials (arterial wall, balloons, and stents), appear to be feasible and accurate. Different stent and balloon designs and material properties, as well as plaque material properties (e.g., fibrous, fibrofatty, calcified) can be considered in those simulations. Tailoring bifurcation stenting to the patient's specific geometry and biomechanical environment might help improving clinical outcomes.

SUMMARY

A computational simulation platform for interventional procedures planning is disclosed. In embodiments, the computational simulation platform comprises a computer-implemented method that includes: generating a mesh or meshless three-dimensional (3D) reconstruction of a vessel lumen and a surface of the vessel lumen based on invasive or non-invasive imaging; assigning material properties to the 3D reconstructed surface of the vessel lumen based on the invasive or non-invasive imaging; performing balloon pre-dilation, stenting and balloon post-dilation computational simulations with the 3D reconstructed vessel lumen and surface of the vessel lumen; and assessing stent and vessel morphometric and biomechanical measures based on the computational simulations.

In some embodiments, the assigning of the material properties to the 3D reconstructed surface of the vessel lumen based on the invasive or non-invasive imaging includes: determining wall or plaque thickness, lumen area, plaque eccentricity and plaque constituents based on the invasive or non-invasive imaging; dividing the vessel lumen into sequential zones of plaque material; and assigning a value ranging from purely calcium plaque material to purely lipid plaque material.

In some embodiments, the computer-implemented method further includes: assigning plaque plasticity based on the material properties assigned to the 3D reconstructed surface of the vessel lumen.

In some embodiments, the invasive or non-invasive imaging comprises at least one of: coronary angiography, intravascular ultrasound, optical coherence tomography, computed tomography angiography, or magnetic resonance angiography.

In some embodiments, the computer-implemented method further includes: importing design and material properties of stents and balloons; generating a mesh or meshless model of a stent and balloon based on the imported design and material properties; and positioning the modeled the stent and balloon within the 3D reconstructed vessel lumen.

In some embodiments, the design and material properties of the stents and balloons are imported based on invasive or non-invasive imaging.

In some embodiments, the design and material properties of the stents and balloons are imported from one or more databases including manufacturer-provided data.

In some embodiments, the modeled stent and balloon in their crimped state are computationally positioned and bent in the 3D reconstructed vessel lumen.

In some embodiments, the balloon pre-dilation, stenting and balloon post-dilation computations are computationally simulated using finite element analysis.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

DETAILED DESCRIPTION

The present disclosure is directed to a computational simulation platform for interventional procedures planning. In particular, a computational stenting platform is disclosed with reference to FIGS. 1 through 16. Computational simulations can yield incremental information to the anatomical and functional assessment of coronary artery disease in the catheterization laboratory, guiding percutaneous interventions. Computational stenting models can reproduce controversial "what if" scenarios in a 3D environment and in a cost- and time-effective fashion to elucidate the events occurring during the stenting procedure. Computational stenting can characterize the local biomechanical microenvironment pre- and post-stenting, providing a framework for bifurcation stenting optimization and generating new hypotheses that can be tested clinically.

Several computational studies on stent simulations have been reported to date, the great majority of which have focused on idealized non-bifurcated geometries. Limited computational studies on bifurcation stenting have been reported. These studies computationally simulated 1-stent techniques only in a limited number of cases (<2) using simplified plaque material properties and quantitative comparisons of the simulations to reference vessels were not performed. This disclosure presents a novel platform for fully computational patient-specific stenting.

Figure 1:
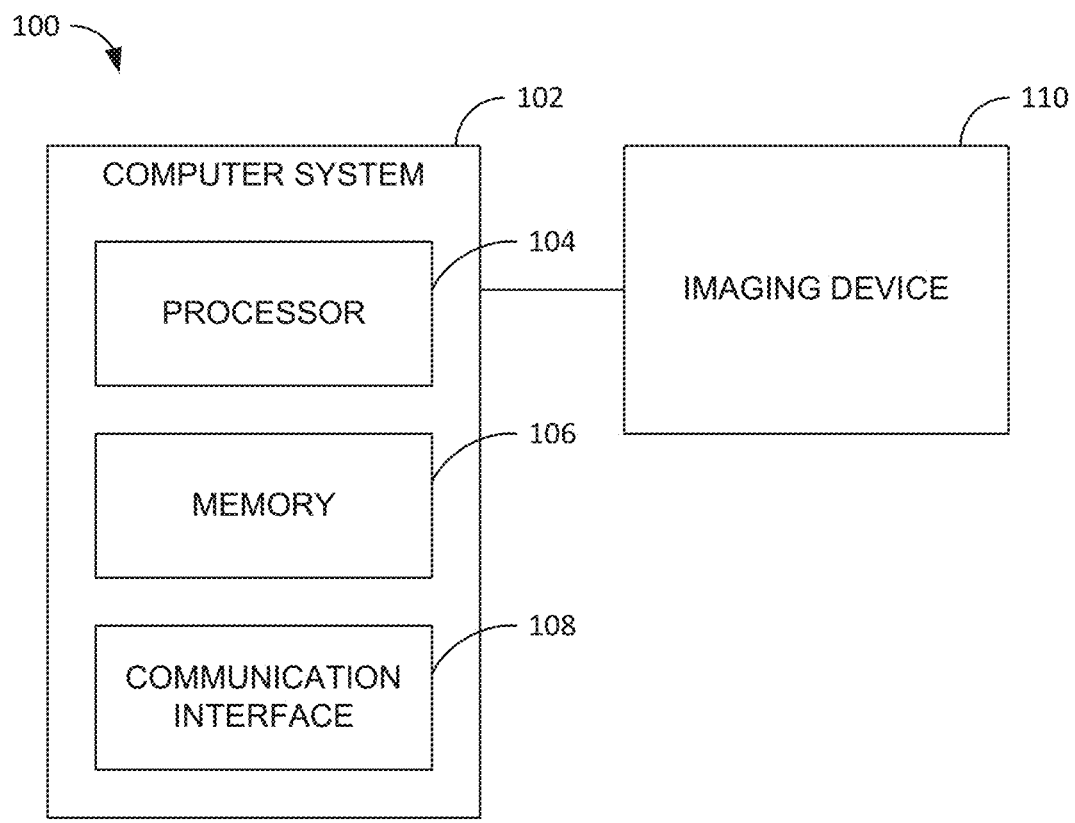
FIG. 1 is a block diagram illustrating a system for simulation and planning of interventional procedures, in accordance with one or more embodiments of this disclosure.

FIG. 1 illustrates a system 100 for simulation and planning of interventional procedures, in accordance with one or more embodiments of this disclosure. The system 100 includes one or more computer systems 102 (e.g., a computer, a plurality of computers performing different steps/processes, and/or a local or cloud computing cluster of computer systems working together sequentially or in parallel). The system 100 further includes one or more invasive or non-invasive medical imaging devices 110 that are communicatively coupled to the one or more computer systems 102. For example, the one or more medical imaging devices 110 may be physically connected (e.g., wired) to the one or more computer systems 102, wirelessly connected (e.g., via WiFi, WLAN, Bluetooth, or the like), and/or communicatively coupled by at least one portable storage device (e.g., USB drive, portable hard drive, or the like) that is configured to store data collected by the one or more medical imaging devices 110 so that the data can be transferred to the one or more computer systems 102.

Examples of an invasive or non-invasive medical imaging device 110 include, but are not limited to, a CT scanner, an X-ray scanner, a fluoroscope, an ultrasound scanner. In embodiments, the one or more invasive or non-invasive medical imaging devices 110 may include any number or combination forgoing devices.

The one or more computer systems 102 may be configured to implement the computational simulation platform by performing various functions, steps and/or operations discussed herein. In embodiments, a computer system 102 (or each computer system 102 of a cluster) includes at least one processor 104, memory 106 and communication interface 108.

The processor 104 provides processing functionality for at least the computer system 102 and can include any number of processors, microprocessors, microcontrollers, circuitry, field programmable gate array (FPGA) or other processing systems and resident or external memory for storing data, executable code and other information accessed or generated by the computer system 102. The processor 104 can execute one or more software programs embodied in a non-transitory computer readable medium (e.g., memory 106) that implement techniques/operations described herein. The processor 104 is not limited by the materials from which it is formed, or the processing mechanisms employed therein and, as such, can be implemented via semiconductor(s) and/or transistors (e.g., using electronic integrated circuit (IC) components), and so forth.

The memory 106 can be an example of tangible, computer-readable storage medium that provides storage functionality to store various data and/or program code associated with operation of the computer system 102/processor 104, such as software programs and/or code segments, or other data to instruct the processor 104, and possibly other components of the computer system 102, to perform the functionality described herein. Thus, the memory 106 can store data, such as a program of instructions for operating the computer system 102, including its components (e.g., processor 104, communication interface 108, etc.), and so forth. It should be noted that while a single memory 106 is described, a wide variety of types and combinations of memory (e.g., tangible, non-transitory memory) can be employed. The memory 106 can be integral with the processor 104, can comprise stand-alone memory, or can be a combination of both. Some examples of the memory 106 can include removable and non-removable memory components, such as random-access memory (RAM), read-only memory (ROM), flash memory (e.g., a secure digital (SD) memory card, a mini-SD memory card and/or a micro-SD memory card), solid-state drive (SSD) memory, magnetic memory, optical memory, universal serial bus (USB) memory devices, hard disk memory, external memory, and so forth.

The communication interface 108 can be operatively configured to communicate with components of the computer system 102. For example, the communication interface 108 can be configured to retrieve data from the processor 104 or other devices (e.g., medical imaging devices 110, other computer systems 102, local/remote servers, etc.), transmit data for storage in the memory 106, retrieve data from storage in the memory 106, and so forth. The communication interface 108 can also be communicatively coupled with the processor 104 to facilitate data transfer between components of the computer system 102 and the processor 104. It should be noted that while the communication interface 108 is described as a component of the computer system 102, one or more components of the communication interface 108 can be implemented as external components communicatively coupled to the computer system 102 via a wired and/or wireless connection. The computer system 102 can also include and/or connect to one or more input/output (I/O) devices (e.g., via the communication interface 108), such as an input device (e.g., a mouse, a trackball, a trackpad, a joystick, a touchpad, a touchscreen, a keyboard, a keypad, a microphone (e.g., for voice commands), etc.) and/or an output device (e.g., a display, a speaker, a tactile feedback device, etc.). In embodiments, the communication interface 108 may also include or may be coupled with a transmitter, receiver, transceiver, physical connection interface, or any combination thereof.

It shall be understood that any of the functions, steps or operations described herein are not necessarily all performed by one computer system 102. In some embodiments, various functions, steps, or operations may be performed by one or more computer systems 102. For example, one or more operations and/or sub-operations may be performed by a first computer system, additional operations and/or sub-operations may be performed by a second computer system, and so forth. Furthermore, some of the operations and/or sub-operations may be performed in parallel and not necessarily in the order that they are disclosed herein.

Figure 2:
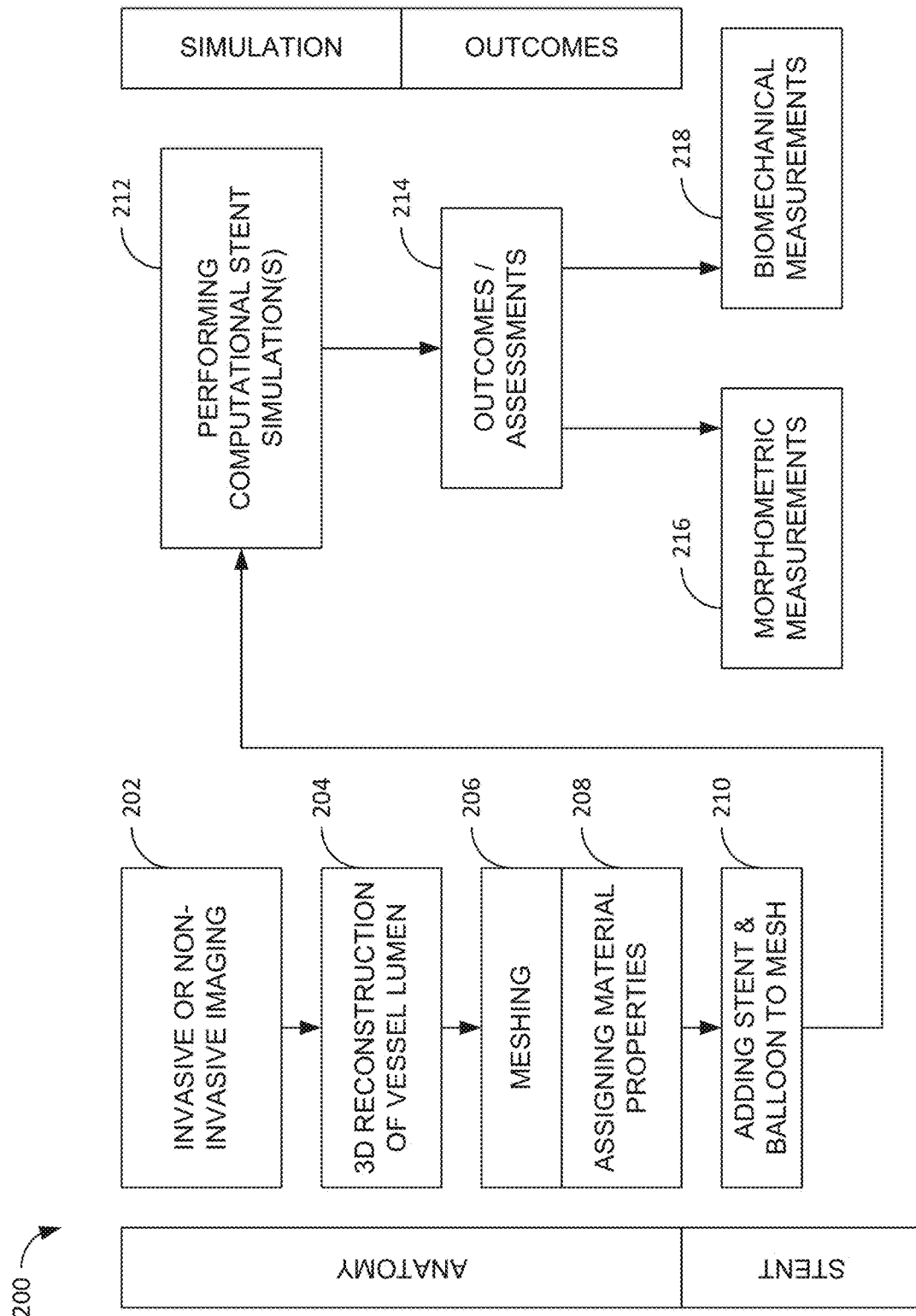
FIG. 2 is a flow diagram illustrating a computational simulation platform for interventional procedures planning, in accordance with one or more embodiments of this disclosure.

FIG. 2 is a flow diagram illustrating a computational simulation platform 200 for interventional procedures planning. In embodiments, the computational simulation platform 200 is embodied by a computer-implemented method that includes the following blocks (e.g., functions, steps and/or operations).

At block 202, invasive or non-invasive imaging data is collected for one or more vessels (e.g., a coronary artery bifurcation or any other vasculature or portion thereof). For example, the one or more computer systems 102, via the one or more imaging devices 110, may be configured to collect invasive imaging data (e.g., via coronary angiography, intravascular ultrasound and/or optical coherence tomography) and/or non-invasive imaging data (e.g., via computed tomography angiography and/or magnetic resonance angiography) associated with one or more vessels. It is further contemplated that hybrid or semi-invasive techniques may also be used. Additionally, the one or more computer systems 102, via the one or more imaging devices 110, may be configured to collect invasive imaging data and/or non-invasive imaging data associated with one or more vessels using any of the tools and/or techniques described in the example embodiments (e.g., Examples 1-3) discussed below.

At block 204, a 3D reconstruction of at least one vessel lumen (e.g., a coronary artery bifurcation or any other vasculature or portion thereof) and a surface of the vessel lumen (e.g., the lumen wall and/or any plaque built up on the lumen wall) is generated based on the invasive or non-invasive imaging data collected by the one or more imaging devices 110. For example, the one or more computer systems 102 may be configured to generate a 3D reconstruction of a bifurcation lumen and wall/plaque based on an invasive (e.g., angiography, optical coherence tomography or intravascular ultrasound) or non-invasive (computed tomography angiography or magnetic resonance angiography) imaging modality or any combination of these modalities. Special emphasis is put on reconstructing the true dimensions (thickness, eccentricity) of the arterial wall and plaque. Furthermore, the 3D reconstructed bifurcation is patient-specific. Additionally, the one or more computer systems 102 may be configured to generate the 3D reconstruction of at least one vessel lumen (e.g., a coronary artery bifurcation or any other vasculature or portion thereof) and a surface of the vessel lumen (e.g., the lumen wall and/or any plaque built up on the lumen wall) based on the invasive or non-invasive imaging data collected by the one or more imaging devices 110 using any of the tools and/or techniques described in the example embodiments (e.g., Examples 1-3) discussed below.

Optionally, at block 206, a mesh of the 3D reconstructed vessel lumen and surface of the vessel lumen is generated.

For example, the one or more computer systems 102 may be configured to generate a mesh of the 3D reconstructed vessel lumen and surface of the vessel lumen using any of the tools and/or techniques described in the example embodiments (e.g., Examples 1-3) discussed below. In some embodiments of the computational simulation platform, the 3D reconstructed vessel lumen and surface of the vessel lumen are not meshed. In this regard, the 3D reconstructions themselves may be used to perform balloon pre-dilation, stenting and balloon post-dilation computational simulations.

At block 208, material properties are assigned to the 3D reconstructed surface of the vessel lumen. For example, the one or more computer systems 102 may be configured to assign material properties to the 3D reconstructed surface of the vessel lumen based on invasive or non-invasive imaging data collected by the one or more imaging devices 110. Realistic material properties can be assigned to the arterial wall and plaque based on imaging data received from the one or more medical imaging devices 110. This may include broad coverage of materials from lipid to fibrous and calcified, including a wide range of combinations between these materials. In some embodiments, the one or more computer systems 102 are configured to assign material properties to the 3D reconstructed surface of the vessel lumen by determining wall or plaque thickness, lumen area, plaque eccentricity and plaque constituents based on invasive or non-invasive imaging. In some embodiments, the one or more computer systems 102 are further configured to assign material properties to the 3D reconstructed surface of the vessel lumen by dividing the vessel lumen into sequential zones of plaque material and assigning a value (e.g., a quarter number or any other incremental value) ranging from purely calcium plaque material to purely lipid plaque material. In some embodiments, the one or more computer systems 102 are configured to assign plaque plasticity based on the material properties assigned to the 3D reconstructed plaque. Additionally, the one or more computer systems 102 may be configured to assign material properties to the 3D reconstructed surface of the vessel lumen based on invasive or non-invasive imaging data collected by the one or more imaging devices 110 using any of the tools and/or techniques described in the example embodiments (e.g., Examples 1-3) discussed below.

At block 210, design and material properties of stents and balloons are imported and used to generate a model (e.g., a mesh or other computational model) of a stent and balloon. The true stent design and materials, as well as realistic pre- and post-dilatation balloon geometries with compliant, semi-compliant and non-compliant properties are incorporated in the computational platform 200. For example, the one or more computer systems 102 may be configured to import design and material properties of the stents and balloons based on invasive or non-invasive imaging data received from the one or more medical imaging devices 110. Alternatively, or additionally, the one or more computer systems 102 may be configured to import design and material properties of the stents and balloons from one or more databases including manufacturer-provided data. The one or more computer systems 102 may be configured to generate a model of a stent and balloon, preferably with structured mesh, using any of the tools and/or techniques described in the example embodiments (e.g., Examples 1-3) discussed below. The modeled stent and balloon in their crimped state may be computationally positioned and bent in the 3D reconstructed vessel lumen. In some embodiments, the stents and balloons are bent and positioned in the 3D reconstructed vessel lumen following the true 3D course of the artery. Additionally, the one or more computer systems 102 may be configured to import design and material properties of the stents and balloons, generate a model (e.g., mesh or other computational model) of a stent and balloon, and/or position the modeled stent and balloon within or relative to the 3D reconstructed vessel lumen and surface of the vessel lumen using any of the tools and/or techniques described in the example embodiments (e.g., Examples 1-3) discussed below.

At block 212, computational stent simulations are performed. For example, the one or more computer systems 102 may be configured to perform balloon pre-dilation, stenting and balloon post-dilation computational simulations with the 3D reconstructed vessel lumen and surface of the vessel lumen. In some embodiments, the balloon pre-dilation, stenting and balloon post-dilation computations are computationally simulated using finite element analysis. Preferably, realistic inflation pressures are used. The preload of each step may be the baseline for the next step, thereby causing the lumen and wall expansion to follow realistic patterns. Additionally, the one or more computer systems 102 may be configured to perform balloon pre-dilation, stenting and balloon post-dilation computational simulations with the modeled (e.g., meshed or otherwise modeled) structures using any of the tools and/or techniques described in the example embodiments (e.g., Examples 1-3) discussed below.

At blocks 214 through 218, stent and vessel morphometric and biomechanical measures are assessed based on the computational simulations. For example, the one or more computer systems 102 may be configured to assess morphometric measures including, but not limited to, stent expansion and apposition. The one or more computer systems 102 may be further configured to assess biomechanical measures (e.g., hemodynamic measures) including, but not limited to, fluid and solid stresses in the arterial lumen, wall and stent using computational fluid dynamics and finite element analysis. Additionally, the one or more computer systems 102 may be configured to assess stent and vessel morphometric and biomechanical measures based on the computational simulations using any of the tools and/or techniques described in the example embodiments (e.g., Examples 1-3) discussed below.

The proposed computational stenting platform 200 can yield incremental information to the anatomical and functional assessment of coronary artery disease in the Cath Lab, guiding the percutaneous interventions. Patient-specific computational stenting models can reproduce controversial "what if" scenarios in a 3D environment and in a cost- and time-effective fashion to elucidate the events occurring during the stenting procedure. These models can characterize the local biomechanical microenvironment pre- and post-stenting, providing a framework for stenting optimization and generating new hypotheses that can then be tested clinically. In the era of powerful computers, predictive patient-specific computational simulations of bifurcation stenting are feasible and reliable.

Computational simulations of bifurcation stenting can help the industry to develop new generation stents, ultimately improving clinical outcomes. Stenting simulations have the potential to be used (near) real time to guide bifurcation PCIs (auto-pilot PCI), which might be particularly useful for non-expert interventionalists. The patient-specific computational stenting approach integrates the bifurcation anatomy, disease complexity and biomechanics in a comprehensive scheme. This allows for the generation of a comprehensive atlas of patient bifurcations and simulations of various stenting techniques applied to the entire range of real-world bifurcation geometries. Such a patient bifurcation atlas may help identify favorable stenting techniques for specific groups of bifurcation anatomy and set the stage for real-time decision making in the Cath Lab using machine and deep learning strategies. Also, the proposed computational platform may evolve to a helpful educational and training tool, and finally can be applied to other vascular beds (i.e., carotid artery bifurcation or aortic bifurcation or structural heart disease interventions).

Specific implementations of the computational simulation platform 200 are discussed in the examples and embodiments (e.g., Examples 1-3) discussed below. The following examples and embodiments should not be construed as limitations of the present disclosure, unless otherwise specified in the Claims. In other implementations, equivalent systems, tools, materials, software and/or processes may be employed without deviating from the scope of this disclosure. Furthermore, certain aspects or configurations described with respect to a specific embodiment may be implemented in combination with any aspect or configuration of another embodiment without deviating from the scope of this disclosure.

Example 1—Patient-Specific Bench Stenting

Silicone bifurcation models: Four bench models of patient-specific coronary artery bifurcations were created using an in-house technique. Specifically, the initial bifurcation geometries were 3D reconstructed from human coronary angiograms. For each model, a negative mold was designed and 3D printed with acrylonitrile butadiene styrene (ABS) material. After smoothing the inner surface of the mold using acetone vapor, polydimethylsiloxane (PDMS) was injected into the mold and then put in the oven for curing of PDMS. The physical models were then immersed in an acetone beaker to dissolve the ABS and generate the silicone bifurcation models for bench test.

Contrast enhanced micro computed tomography (μCT) imaging: To acquire high-resolution lumen geometry, all silicone bifurcation models were filled with contrast, and then scanned with μCT (e.g., SkyScan 1172 version 1.5, SKYSCAN, Antwerpen, Belgium) using the following parameters: Image pixel size (26.9 μm), voltage (100 kV), and current (100 μA). The reconstructed 3D models based on μCT before stenting served as anatomical input to computational stent simulations.

Bench stenting of silicone bifurcation models: The silicone bifurcation models were placed in a custom-made flow chamber. A computer-controlled bioreactor circuit was connected to the inlet and outlets of the bifurcation, allowing circulation of 1 L of deionized water at a steady flow-rate of 100 ml/min.

Stereoscopic scanning: All the stents deployed in the silicone bifurcation models were imaged with a stereo microscope (e.g., Olympus SZX16, Tokyo, Japan). The microscopic images were used to measure the distance of the stent edges from fixed points (e.g., carina) and guide the correct positioning of the stents in the computational models.

Computational mesh: The 3D reconstructed lumens by μCT were meshed with four-node quadrilateral shell elements using HyperMesh (Altair Engineering, Troy, MI, USA). The computer-aided design models of stents used in the bench stenting procedures were provided by the manufacturers (Boston Scientific, Maple Groove, MN, USA and Medtronic Vascular, Santa Rosa, CA, USA) at their nominal dimensions. The balloons were computationally created in Grasshopper (plugin to Rhinoceros 6.0, Robert McNeel and Associates, Seattle, WA, USA) at their crimped state. The stents were meshed in HyperMesh using beam elements (Resolute Integrity and Onyx. Medtronic) or hexahedral elements (Synergy, Boston Scientific), whereas the balloons were meshed with quadrilateral finite-membrane-strain elements.

Material properties: The cured silicone samples were cut into rectangular specimens and underwent uni-axial compression testing. The obtained force-displacement curves were converted into strain-stress curves. The Neo-Hookean hyperelastic model was used to fit the non-linear strain-stress curve. A specific thickness was assigned to the shell elements of each bifurcation to represent the true thickness of the silicone models. The elastic modulus for compliant, semi- and non-compliant balloons was defined as 300 MPa, 900 MPa and 1,500 MPa, respectively.

Stent and balloon crimping, positioning, and bending: The correct stent and balloon positioning in the computational bifurcation models was determined by angiography, μCT and stereoscopic images of the stented silicone models. The stents were first crimped from their nominal states by using surface elements driven by radial displacement. The crimped stents and balloons were positioned and bent along the artery centerline.

Computational simulation of bench stenting procedures: The bench stenting procedures were simulated through a multi-step, quasi-static finite element analysis using the central difference method (Abaqus/Explicit solver). The edges of the bifurcation lumen were fixed to avoid rigid body motion. The balloon edges were constrained to eliminate their motion in all the directions. To model the interactions between different elements (balloon-stent, stent-lumen, balloon-lumen, balloon-balloon), the robust general contact algorithm was used with a friction coefficient of 0.2. The real inflation pressures, which were used in each procedural step, were applied onto the inner surface of the corresponding balloons. The stressed configurations of lumen and stent after each step were used as the initial condition for the next step. Given the very large number of elements and complicated contacts in the computational model, a computer cluster (452 Intel Xeon E5-2670 2.60 GHz 2 CPU/16 cores and 64 GB RAM per node University of Nebraska) was used to perform the high-speed computational simulations.

Training of computational bench stenting: The 3D reconstructed bifurcation and stent geometry by μCT post-stenting served as ground truth for the training of computational stenting. The simulated bifurcation and μCT bifurcation were co-registered using the bifurcation carina as fixed point. The mean lumen diameter (MLD) was used for the comparison studies.

Figure 4:
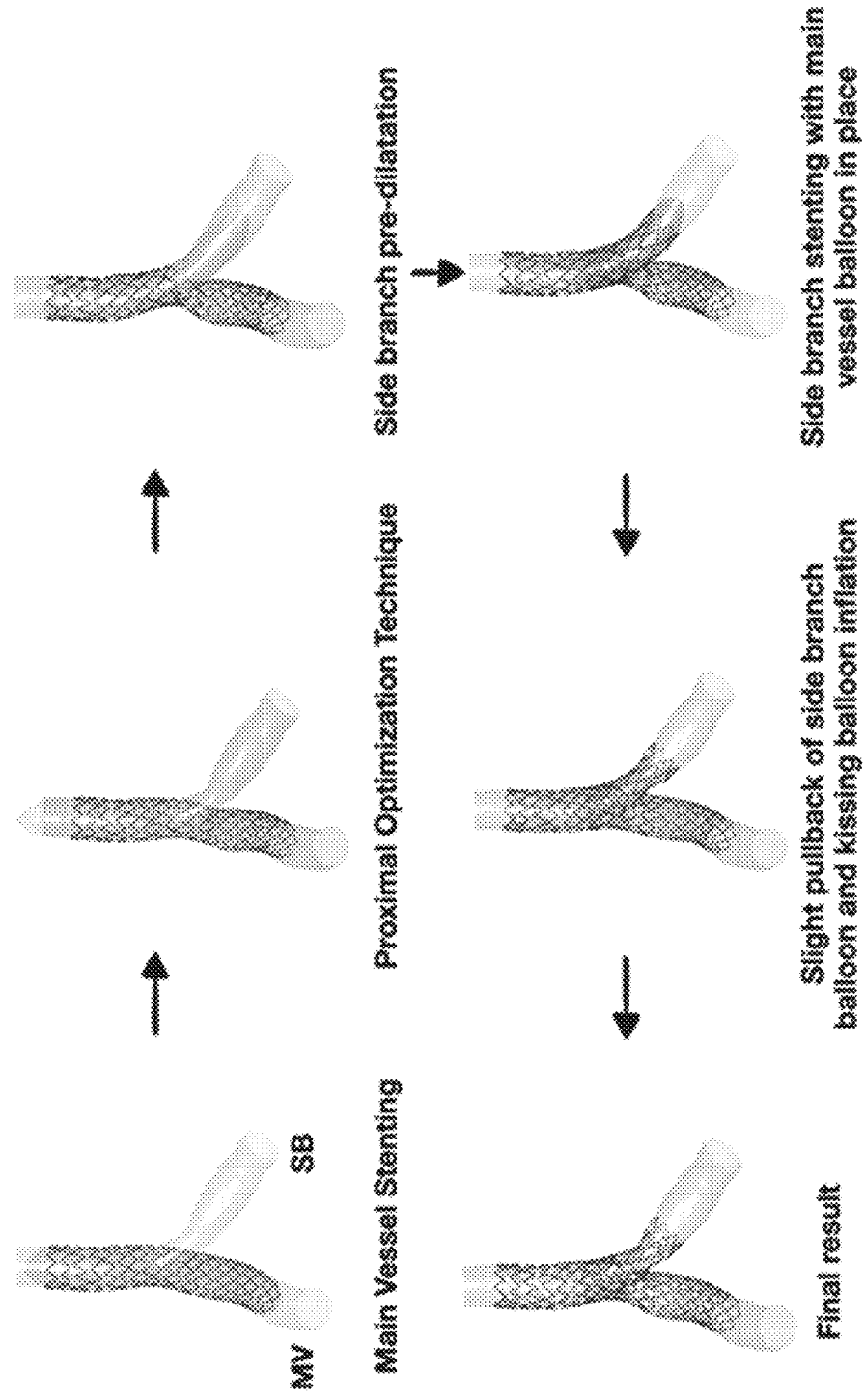
FIG. 4 illustrates a process for computational simulation bench stenting in a patient-specific bifurcation, in accordance with one or more embodiments of this disclosure.
Figure 5:
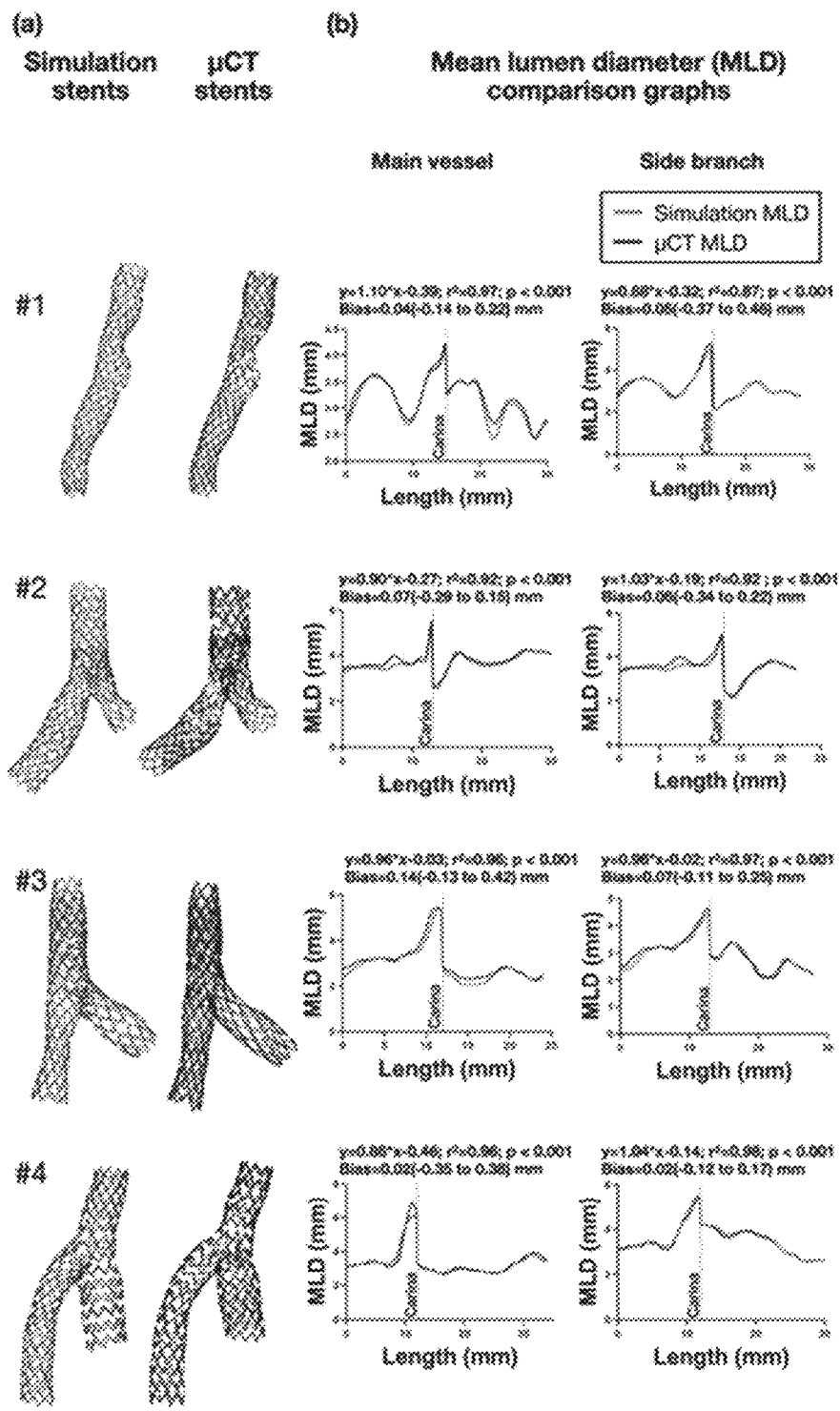
FIG. 5 illustrates results of a comparison of stenting simulation results against a micro computed tomography (μCT)-reconstructed model, in accordance with one or more embodiments of this disclosure.

Results: All bench stenting procedures, the majority of which were multi-step two stent techniques, were successfully simulated. FIG. 4 illustrates a representative example of T-and-Protrusion (TAP) technique with two stents. Visually, the computationally simulated stents were nearly identical in size and shape to the actual μCT-reconstructed stents (FIG. 5, (a)). The MLD was plotted along the axial direction of the simulated and μCT reconstructed stents (FIG. 5, (b)), and quantitatively compared between methods with Bland Altman analysis that yielded a minimal mean difference of 0.02 (−0.12 to 0.17) mm.

Figure 6:
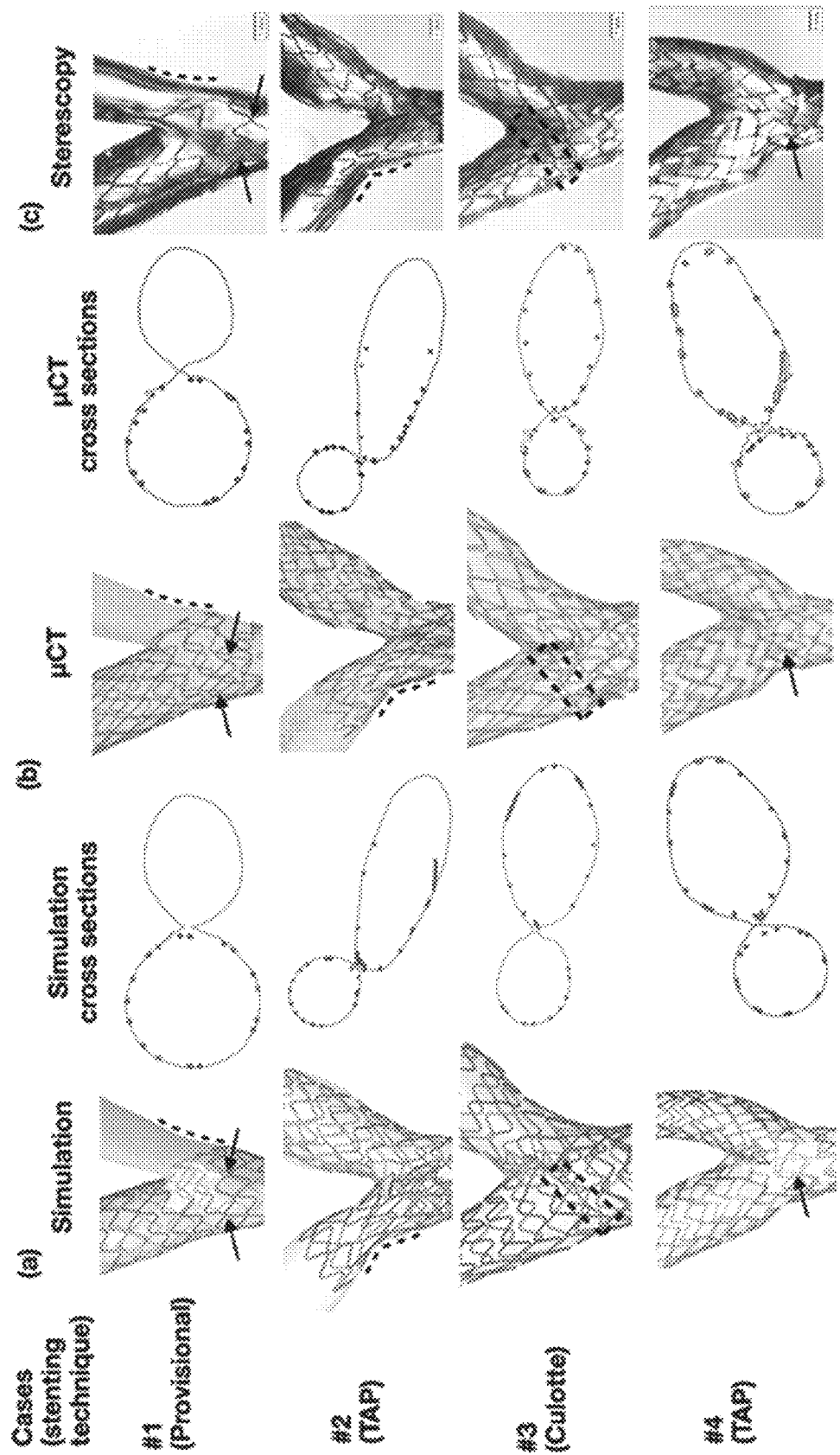
FIG. 6 illustrates results of a qualitative comparison of computational stenting simulation of bench bifurcation models, in accordance with one or more embodiments of this disclosure.

Contrast enhanced μCT and stereoscopic images further revealed the ability of the disclosed computational stenting platform to replicate with high precision fine details of the bench stenting procedures, including malapposed struts, side branch ostium size and shape, and gaps in struts around the anatomically sensitive site of carina (FIG. 6).

Example 2—Clinical Stenting

Figure 3:
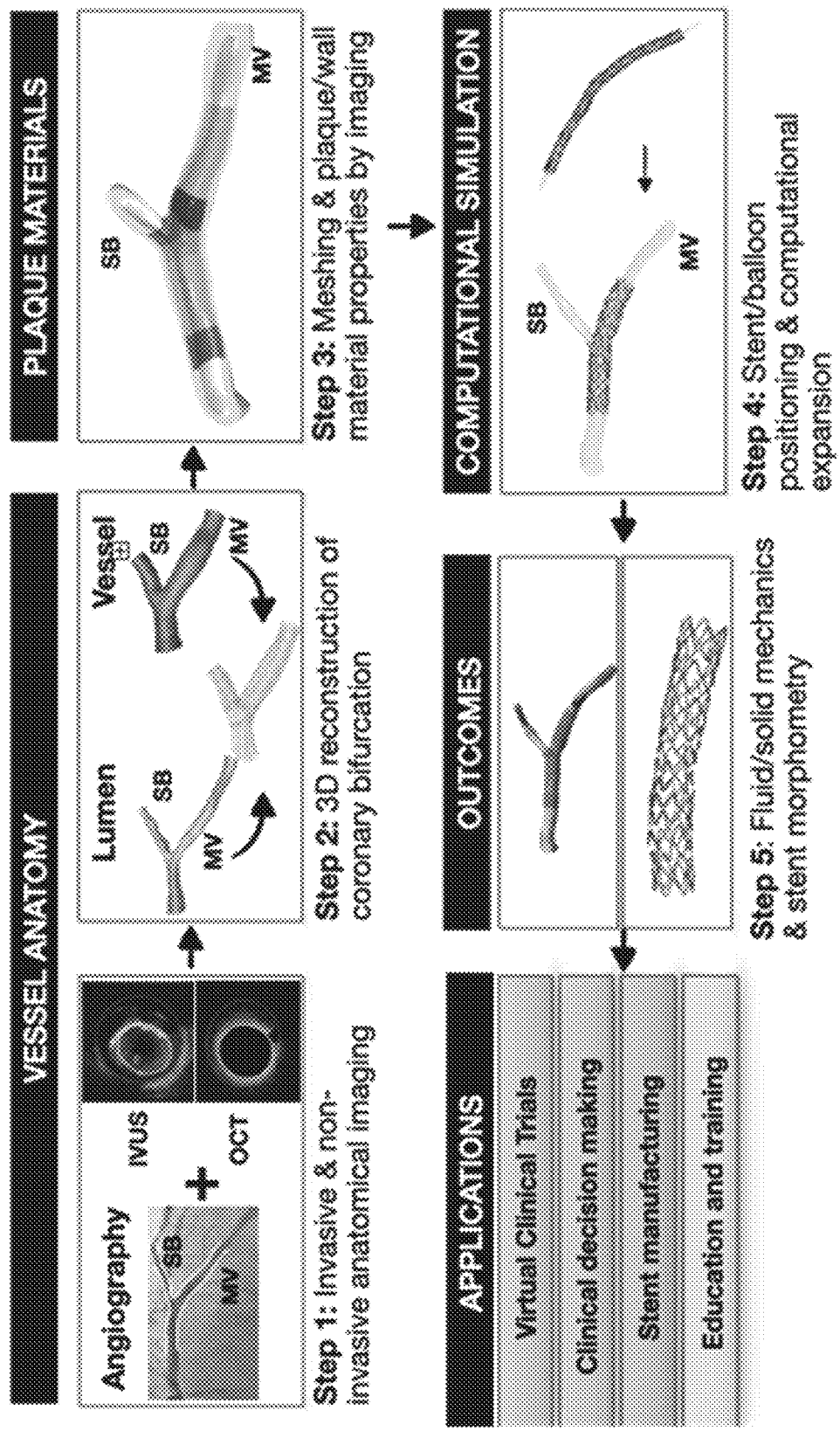
FIG. 3 is a flow diagram illustrating workflow of clinical bifurcation stenting simulations, in accordance with one or more embodiments of this disclosure.

Patient data: Seven patient cases were selected for the patient-specific computational simulations from the PRO-POT (Randomized trial of the proximal optimization technique in coronary bifurcation lesions, IRB approval number 15-159-2), a multi-center, prospective, open-label study that compared proximal optimization technique vs. kissing balloon inflation in provisional stenting of coronary bifurcations using Zotarolimus-eluting stents (Resolute Integrity or Onyx, Medtronic). All patients underwent coronary angiography at multiple angiographic planes and intracoronary imaging with OCT of main vessel (MV) and side branch (SB) before percutaneous coronary interventions (PCI), immediately post stenting, and at the end of the procedure. Pre-PCI anatomical imaging data were used to 3D reconstruct the patient-specific coronary bifurcation anatomies which served as anatomical input to the computational stenting simulations. The workflow for computational simulations of clinical bifurcation stenting is illustrated in FIG. 3.

Training group: Five out of seven cases were used for training of the computational stenting platform, wherein none of the operators were blinded. All the PCI steps performed in this group of cases were replicated in the computational environment. The post-PCI OCT data were used as ground truth for the comparison to the computational simulations.

Testing group: Two cases were chosen for testing of the computational stenting platform. The operators responsible for angiography and OCT imaging analysis, 3D reconstruction of vessels, computational stenting simulations and comparison studies were blinded to each other. The stenting simulation results were compared with the post-PCI OCT imaging.

3D reconstruction of bifurcation geometry: The pre-PCI bifurcation geometries were 3D reconstructed from fusion of angiography and OCT, as previously described. Briefly, the bifurcation centerline was generated from two angiographic planes (Pie Medical Imaging BV, Maastricht, Netherlands), and served as the backbone of the reconstruction. The segmented OCT images (EchoPlaque 4.0, Indec, Los Altos, CA, USA) were aligned along the centerline using the carina as reference point. A step-wise approach was followed for the delineation of the outer borders in OCT images, as previously described. The disclosed approach worked successfully in >95% of images and involved the following steps: (i) in case of ill-defined outer wall borders, the outer wall was limited at the margin of the complete signal loss; (ii) in case the margin of complete signal loss could not be identified in <180 degrees of vessel circumference, the visible outer wall border was interpolated; and (iii) in case the margin of complete signal loss could not be identified in >180 degrees of vessel circumference, that particular OCT frame was discarded and an adjacent frame was segmented following the same steps (i-ii). The aligned lumen and wall contours were lofted to build the MV and SB inner and outer surfaces, and the MV and SB surfaces were finally merged to create the pre- and post-PCI bifurcation lumen and wall.

Computational mesh: The 3D reconstructed bifurcation models were meshed with hexahedral elements (ICEM CFD 17.2, ANSYS, Inc., Canonsburg, PA, USA). The stent design models were provided by the manufacturer (Medtronic Vascular, Santa Rosa, CA, USA) at their nominal dimensions. The balloons were constructed in Grasshopper at their crimped state. The stents and balloons were meshed using fully hexahedral and quadrilateral finite-membrane-strain elements, respectively.

Material properties: In computational simulations, the wall thickness, lumen area, plaque eccentricity and plaque material were determined by OCT. A novel plaque scoring system was established based on the experimental data represented by the stress/strain graph of sixth order polynomial coefficients. The area, circumference and thickness of lipid, fibrous and calcified material were assessed in each OCT frame of MV and SB pullback by an imaging expert (YSC). Of note the imaging expert was blind to the simulation results of the testing group. Then, the MV and SB were divided into sequential zones of homogeneous plaque material. Each zone was assigned a quarter number (e.g., −0.25, 0, +0.25, etc.) ranging from +2 (calcium only) to −2 (lipid only). Fibrolipid plaques with predominant lipid were assigned a score of −0.75 or −0.5, fibrolipid plaques with necrotic core −0.25, fibrous plaques 0, fibrolipid plaques with predominant fibrous +0.25, fibrocalcific plaque with moderate calcium +0.5, fibrocalcific plaque with severe calcium +0.75 or +1. Normal wall thickness and tapering were assessed by OCT. The normal wall material was modeled using sixth-order reduced polynomial constitutive equation to characterize the isotropic hyper-elastic mechanical behavior, as previously described. The coefficients for arterial media layer were obtained by fitting the equation to the experimental data. Wall plasticity ranging from 19-25% was assigned based on the material properties. The cobalt alloy MP35N of Resolute Integrity and Onyx was modeled with the Von Mises-Hill plasticity model with isotropic hardening, while the Pt—Ir alloy core of Resolute Onyx was modeled with perfect plasticity. The balloons were modeled as pure linear elastic material with the same material properties as in the simulations of bench group.

Stent and balloon crimping, positioning, and bending: All stents were first crimped from their nominal states using surface elements driven by radial displacement. The crimped stents and balloons were positioned and bent along the centerline (FIG. 3). The stent and balloons were precisely positioned in the bifurcations by referring to fiduciary markers (e.g., radiopaque markers of stent/balloons, carina, and intersection points of guidewires) on the angiography and OCT.

Computational simulations: All the steps of PCI procedures were computationally replicated through a multi-step, large-deformation, quasi-static finite element analysis using the central difference method (Abaqus/Explicit solver). The boundary conditions and simulation parameters are described above. The computer cluster above was used to perform the computational simulations.

3D stent reconstruction from OCT: The stents were 3D reconstructed from OCT and angiographic images using a custom-built Grasshopper Python code. First, the stent struts were segmented as individual points and flattened to 2D surfaces. Using the 2D stent design pattern as reference, the stent points were connected by lines that represented the centerlines of stent struts and links. The 2D stent centerlines were wrapped and mapped back to the 3D lumen centerline, and then the volume of stent struts was added.

Computational fluid dynamic (CFD) studies: The post-computational PCI bifurcation geometries were used to discretize the fluid domain for CFD analyses (FIG. 3). The fluid domain was meshed with tetrahedral elements using ICEM CFD (ANSYS Inc., Canonsburg, PA, USA). Transient CFD simulations were performed by means of Fluent (ANSYS Inc.). Pulsatile flow was applied at the inlet of each artery. The Huo-Kassab (HK) law was used to derive the relation between the diameter ratio of two daughter branches and the flow ratio through the branches. The lumen and stent surfaces were approximated as rigid body, where non-slip boundary conditions were applied. The blood density was considered constant with a value of 1,060 kg/m$^3$. The Carreau model was adopted to consider the non-Newtonian nature of blood. The following values for each parameter were used: $\mu_\infty$=0.0035 Pa·s, $\mu_0$=0.25 Pa·s, $\lambda$=25 s and n=0.25. One full cardiac cycle, divided into 100 time steps with a step time of 0.009 s, was simulated.

Comparison metrics: The final lumen and stent geometries after computational stenting simulations were compared to the lumen and stent cross-sections segmented on post-PCI OCT. The cross-sections from post-PCI OCT were used as reference. The simulated bifurcation and frame number of OCT cross-sections were co-registered using carina as fixed marker. The MLD along the stented MV and the mean stent diameter (MSD) were used as comparison metrics.

Statistical methods: Statistical analysis was performed with the statistical package GraphPad Prism 8.0 (GraphPad Inc., San Diego, CA, USA). Continuous variables were expressed as mean±standard error of mean. Bland-Altman analysis was used for comparison, p value of <0.05 was considered statistically significant.

Figure 7:
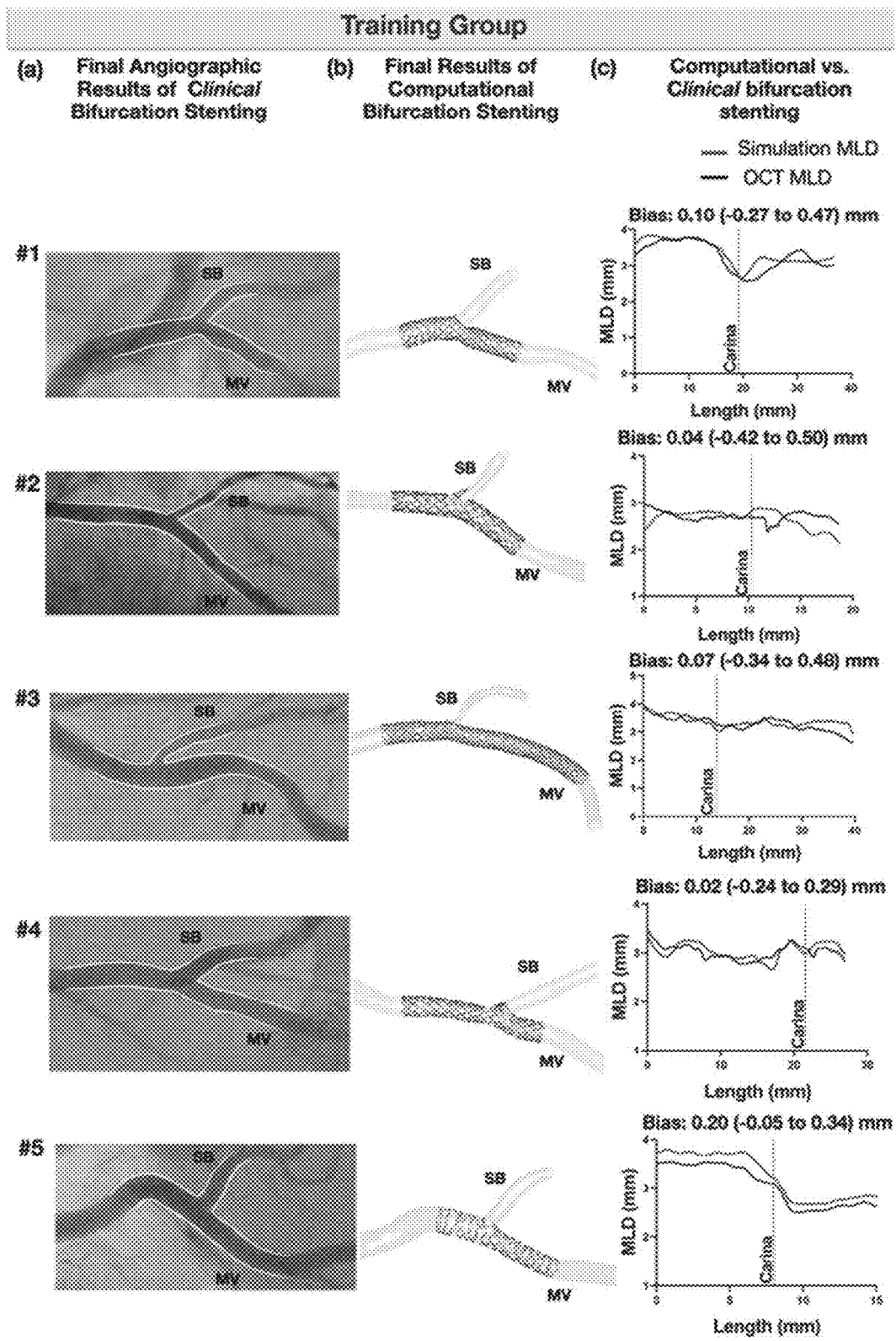
FIG. 7 illustrates results of a morphometric comparison of post-stented lumen, in accordance with one or more embodiments of this disclosure.
Figure 8:
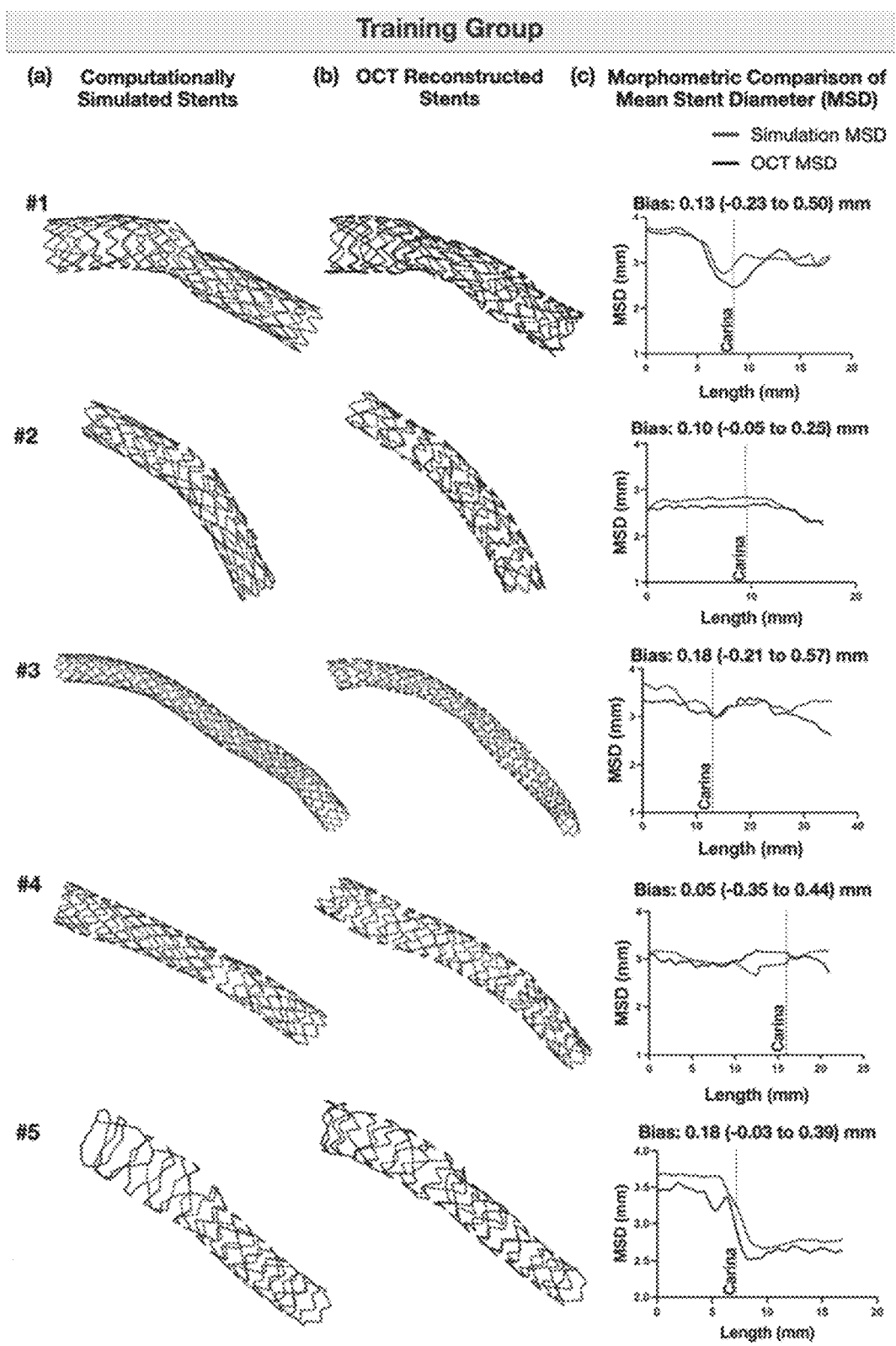
FIG. 8 illustrates results of a morphometric comparison of computational stenting versus reality in clinical cases, in accordance with one or more embodiments of this disclosure.

Training group results: In the training group, clinical stenting procedures, all of which were performed with one stent technique, were successfully simulated with our computational platform. Visually, the computationally stented bifurcation lumen yielded high qualitative agreement with the angiographic lumen post stenting (FIG. 7). Bland Altman analysis revealed MLD differences close to zero [mean bias 0.07 mm (−0.31 to 0.45) mm]. Similarly, the computationally simulated stents exhibited high similarity to the shape and size of the actual stents which were 3D reconstructed by fusing OCT and angiography (FIG. 8, (a) and (b)). The MSD of 16 the computationally simulated stents was quantitatively compared to the OCT stent segmentations, yielding very high agreement [mean bias 0.14 mm (−0.22 to 0.49) mm]. Notably, in Patient #1, the computational simulation replicated the stent under-expansion around the carina secondary to the local stiff plaque material. In Patient #5, the computational stenting reproduced the large gaps between stent struts and consequent over-dilated lumen at the proximal MV following the proximal stent post-dilatation.

Figure 9:
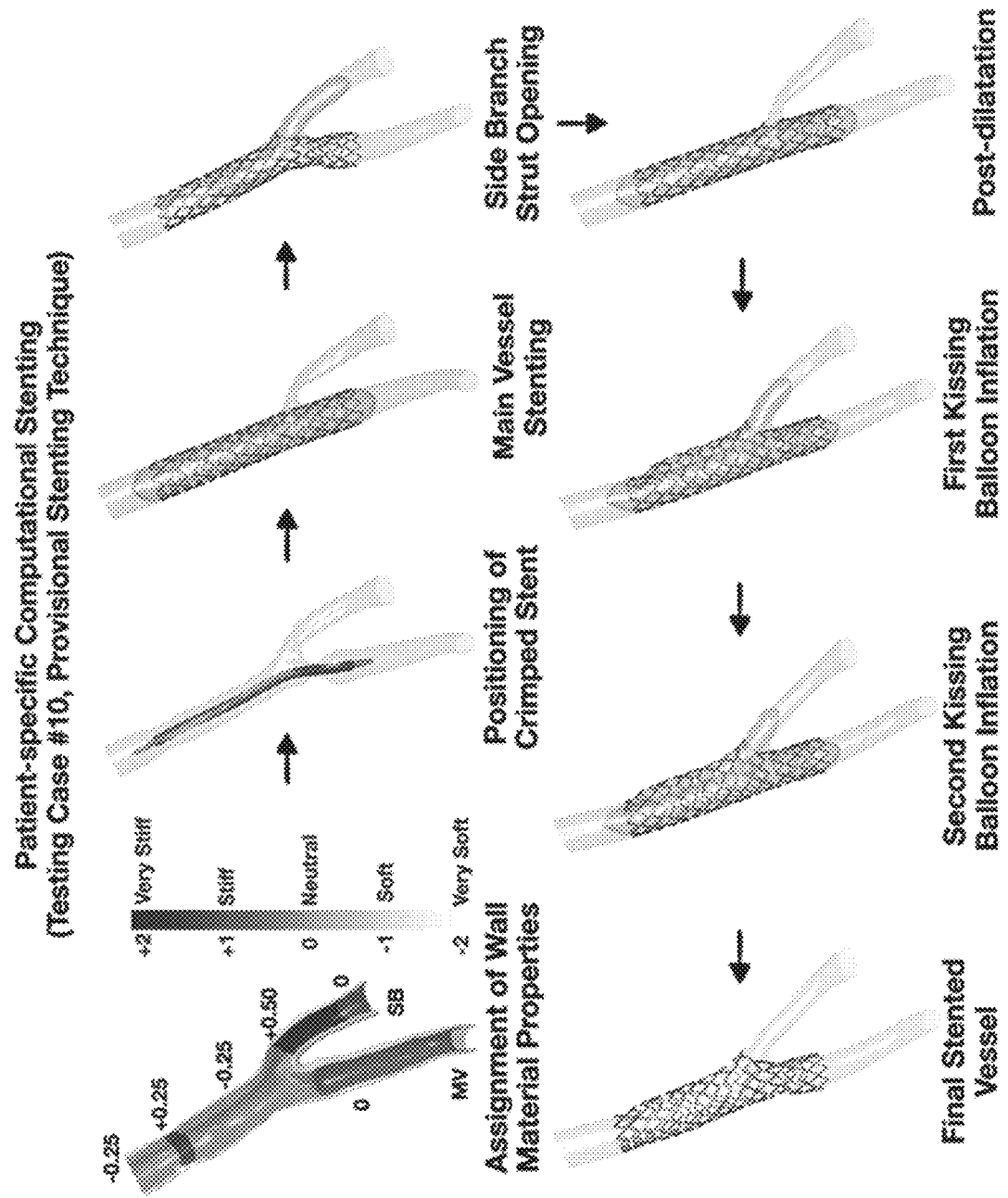
FIG. 9 illustrates a process for computational simulation clinical stenting, in accordance with one or more embodiments of this disclosure.
Figure 10:
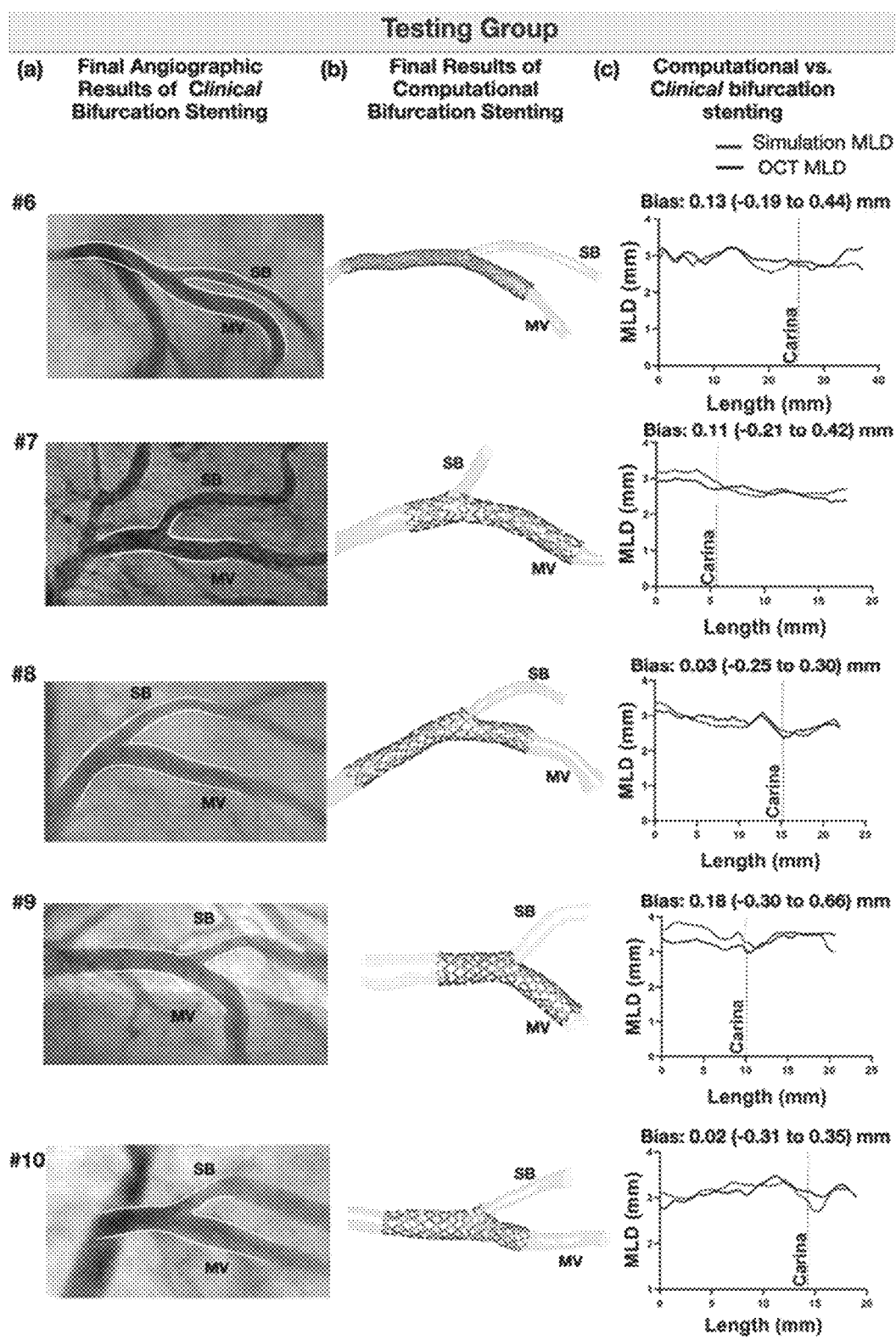
FIG. 10 illustrates results of a morphometric comparison of post-stented lumen, in accordance with one or more embodiments of this disclosure.
Figure 11:
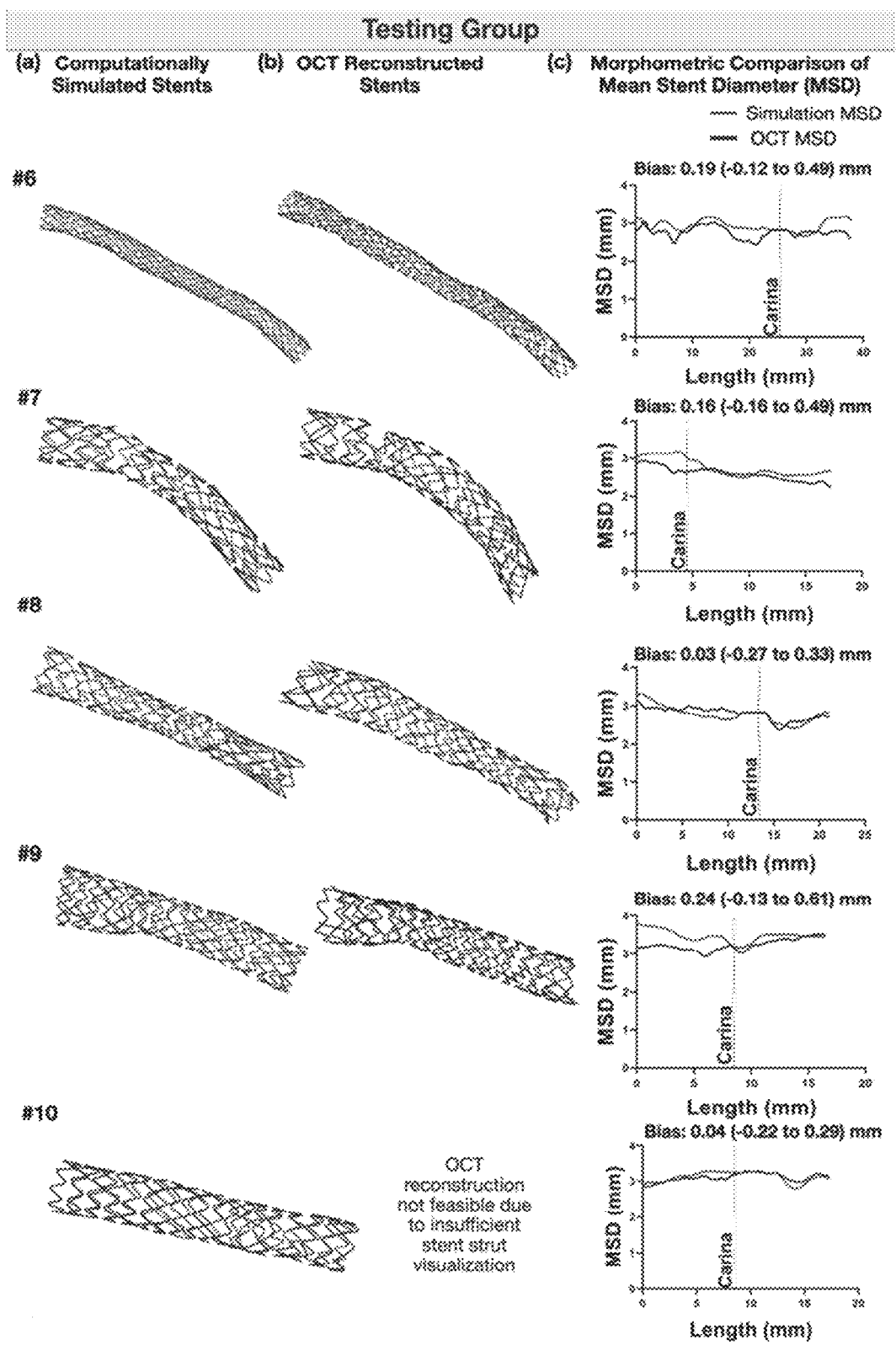
FIG. 11 illustrates results of a morphometric comparison of computational stenting versus reality in clinical cases, in accordance with one or more embodiments of this disclosure.
Figure 12:
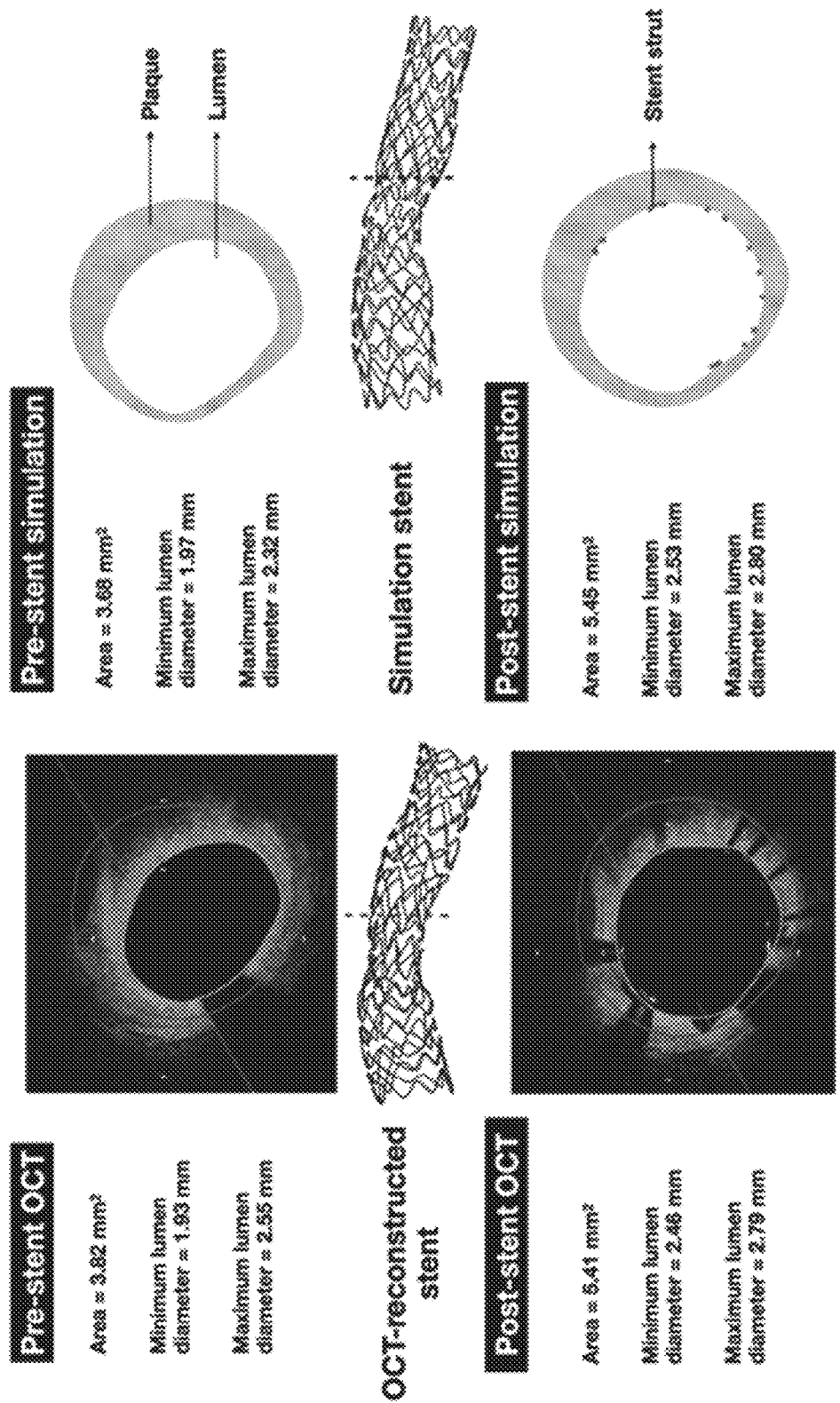
FIG. 12 illustrates results of a morphometric comparison of a single simulation cross-section with optical coherence tomography (OCT) before and after stenting, in accordance with one or more embodiments of this disclosure.

Testing group results: In the testing group, the pre-procedural anatomical information (angiography and OCT) was used to assess the ability of the disclosed computational platform to replicate the clinical stenting (FIG. 9). The computational simulation operators were blinded to the post-procedural OCT. As shown in FIGS. 10 and 11, the computational stenting yielded very high agreement to post-procedural OCT suggesting the robustness of our platform. Quantitative comparisons by Bland-Altman showed small differences in MLD and MSD [mean bias 0.09 mm (−0.29 to 0.46) and 0.13 mm (−0.24 to 0.49) mm, respectively. FIG. 12 provides an example of blinded use of pre-procedural OCT to incorporate the anatomical information of lumen area, plaque thickness and eccentricity into our computational platform and also assign patient-specific material properties in order to achieve realistic computational simulations that yielded similar lumen and stent expansion with the post-procedural OCT.

Figure 13:
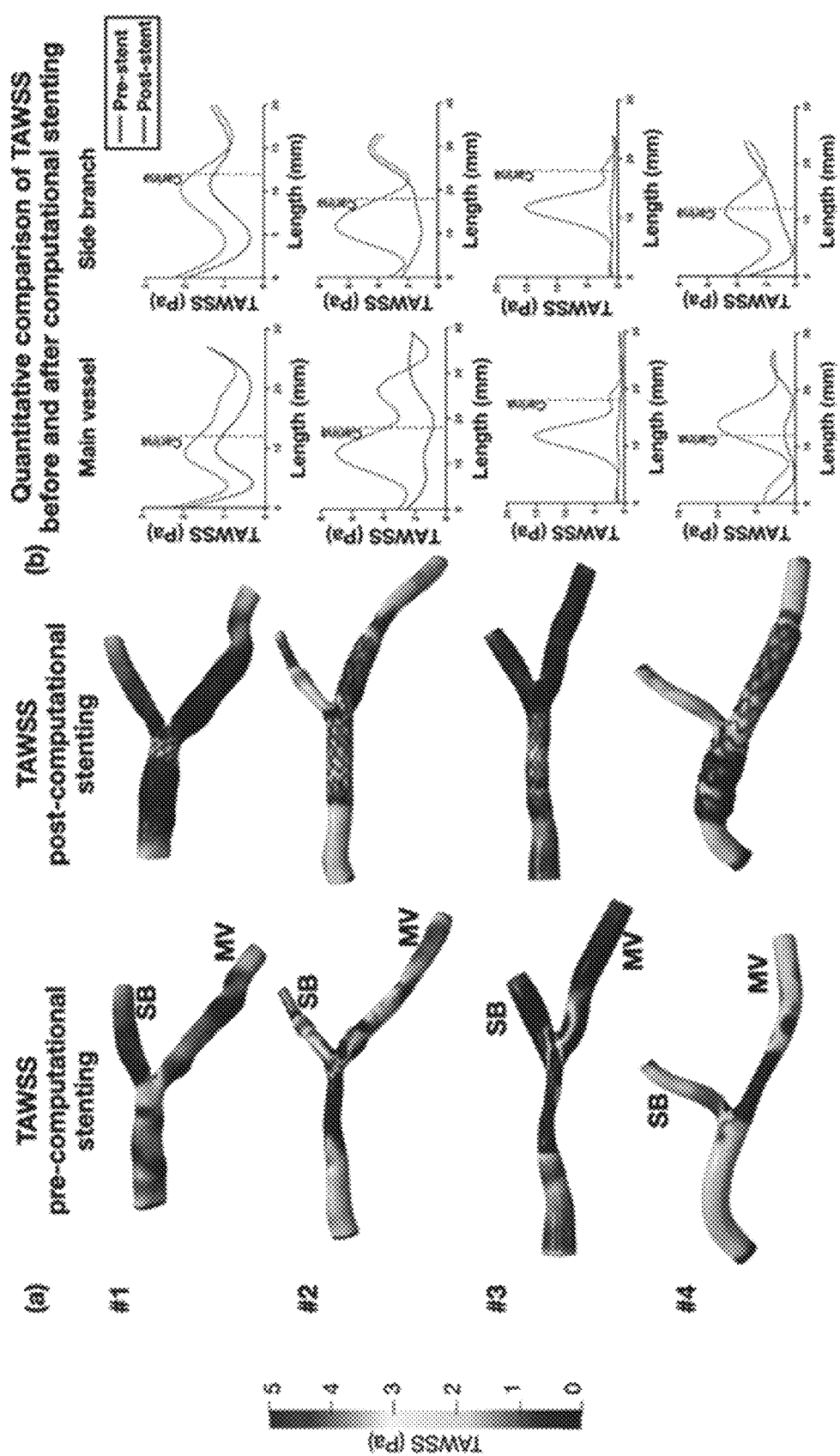
FIG. 13 illustrates results of a computational fluid dynamic study, in accordance with one or more embodiments of this disclosure.

CFD studies: To show the feasibility of CFD in the disclosed simulated procedures, the time-averaged wall shear stress (TAWSS) along the axial direction of MV and SB was compared before and after computational stenting (FIG. 13). As shown quantitatively and qualitatively, stenting normalized the TAWSS in MV.

The proposed computational platform (i.e., computational simulation platform 200) for patient-specific bifurcation stenting simulation provides a reliable resource for clinical research, clinical decision making, stent manufacturing and education on stenting techniques. More specifically, computational stenting can be used in virtual (in-silico) clinical trials using patient-specific anatomical and physiology data and surrogate endpoints (i.e., under-expansion, malapposition, flow dynamics) highly predictive of clinical endpoints. These virtual clinical trials can be adequately powered with large patient data to investigate the performance of different stenting techniques or stent platforms, thereby guiding the actual clinical trials. Flow ISR which is currently underway is an example of such a virtual clinical trial. The study compares different 1- and 2-stent techniques in patient-specific coronary bifurcations. In cardiac catheterization laboratory, computational stenting simulations can be used for pre-procedural planning and decision-making. Computational identification of the optimal stenting and post-dilatation technique that secures the most favorable stent expansion and apposition, as well as hemodynamic microenvironment can provide invaluable guidance to the interventionalist, and possibly increase the procedural success and long-term clinical outcomes (precision medicine). When it comes to stent manufacturers, a cost- and time-effective computational stenting strategy with patient-specific anatomies has the potential to minimize the need for bench and animal research for stent testing. Computational simulations can help with optimization of stent design (e.g., number of crowns and links, strut size) and mechanics (radial and longitudinal strength, expansion capability, vessel scaffolding). The computational approach can effectively evaluate different stent designs in realistic vessel environments obviating the need to manufacture and experimentally test stent prototypes, significantly reducing the development time and manufacturing costs. Another important consideration with computational stenting is that it can be used as an educational tool to train staff and physicians on bifurcation stenting techniques. Mixed reality technologies can further assist towards this direction. Finally, computational bifurcation stenting can be translated to other vascular beds (e.g., carotid, renal or aortic bifurcations).

Coronary artery bifurcations represent unique anatomical locations in the epicardial coronary tree with increased susceptibility to coronary artery disease. Specific anatomic features of bifurcations, including the angle and diameter of the main vessel (MV) and side branch (SB), have a significant impact on the local hemodynamic milieu and subsequent propensity to atherosclerosis. The bifurcation anatomy and extent of disease are substantial determinants of bifurcation stenting strategies and clinical outcomes. Three-dimensional (3D) representation of the bifurcation anatomy and disease burden could help us better appreciate the anatomical complexity of bifurcation disease and optimize the disclosed stenting strategies.

Dedicated single-modality 3D reconstruction of coronary bifurcations can be performed with either 3D quantitative coronary angiography (3D QCA) or coronary computed tomography angiography (CTA). However, both these modalities have major limitations: 3D QCA cannot provide the correct geometrical information of the bifurcation lumen due to the inherent assumptions related to the use of two 2D angiographic planes. Nevertheless, 3D QCA provides accurate details on the 3D course of the bifurcation centerline. Coronary CTA is limited by heart and lung motion artifacts and coronary calcifications, resulting in the exclusion of a descent portion of patients. Hybrid multi-modality 3D reconstruction of bifurcations based on the fusion of intravascular ultrasound (IVUS) or optical coherence tomography (OCT) of the MV only with coronary CTA or invasive angiography has been described. These approaches have limitations mostly related to the accuracy of SB reconstruction. Notably, the use of different imaging modalities for MV and SB reconstruction results in inaccuracies in the reconstruction of the geometrically sensitive and clinically important bifurcation carina and SB. Also, using invasive imaging (IVUS) for the reconstruction of MV and non-invasive imaging (CTA) for the reconstruction of SB is not easily applicable in the clinical setting.

This disclosure builds upon the current state-of-the-art and proposes a novel strategy for the 3D reconstruction of coronary bifurcations based on the fusion of invasive coronary angiography—which provides the bifurcation centerline—with OCT of both MV and SB. Studies described herein were performed: (i) to describe the methodology for 3D reconstruction of coronary bifurcations; and (ii) to systematically test the accuracy, feasibility, and reproducibility of the method in patient-specific silicone bifurcation models, as well as in patient coronary artery bifurcations with varying degrees of disease.

Example 3-3D Reconstruction of Coronary Artery Bifurcations

Figure 14:
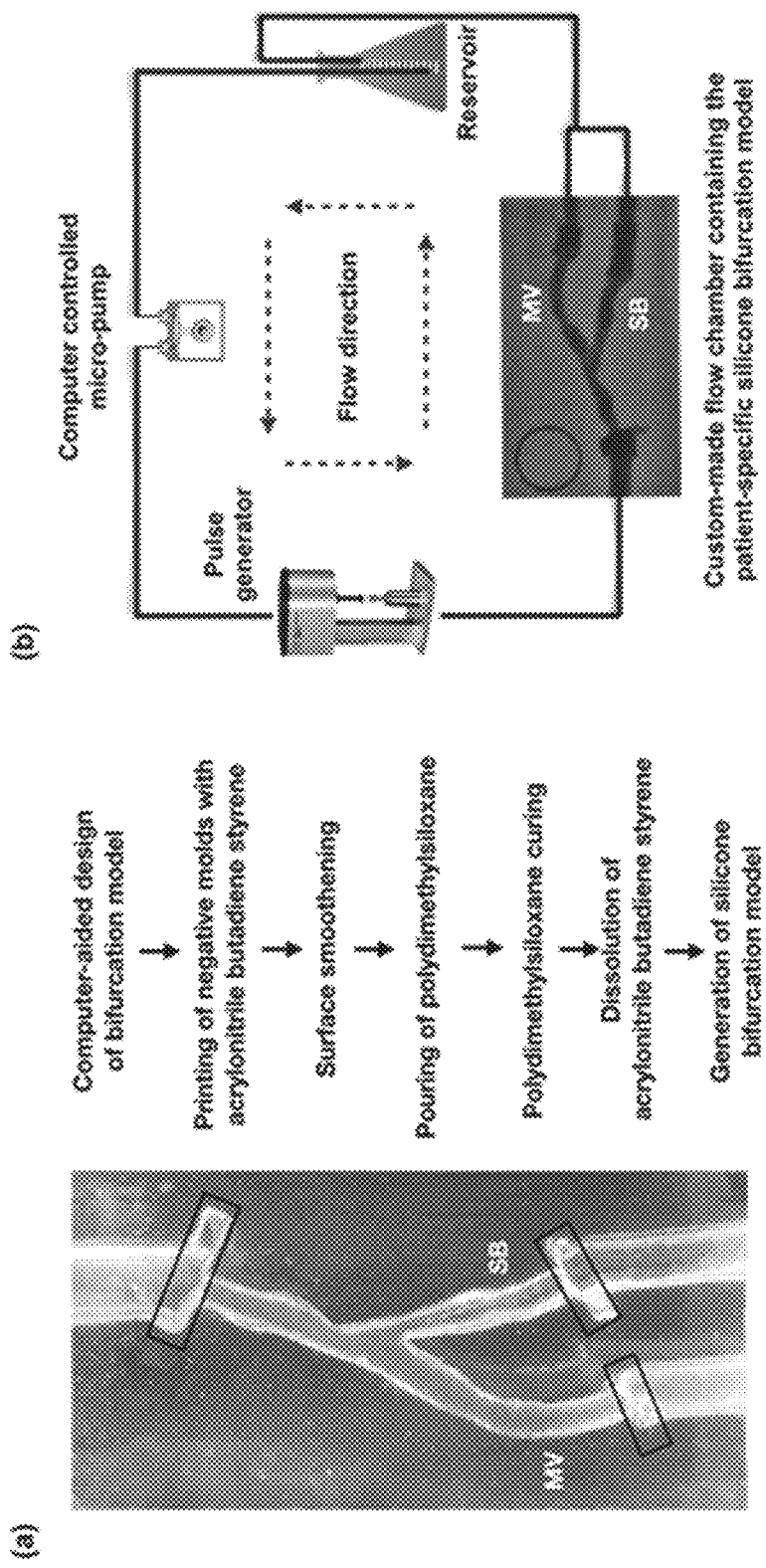
FIG. 14 illustrates patient-specific silicone bifurcation models and a bioreactor flow circuit, in accordance with one or more embodiments of this disclosure.

Silicone models: Five patient-specific silicone models of coronary artery bifurcations were 3D reconstructed, using the disclosed algorithm. The bifurcation geometries were 3D reconstructed from human coronary angiograms during the diastolic phase of the cardiac cycle, using commercially available software (3D CAAS Workstation 8.2, Pie medical imaging, Maastricht, The Netherlands). A flow diagram of the process is illustrated in FIG. 14, (a). To demarcate the region of interest and stabilize the silicone models during the imaging procedures, tube-like extensions and fixed markers were added at the inlet and outlet of the reconstructed bifurcations using a computer-aided design software (Rhinoceros 6, Robert McNeel & Associates, Seattle, USA). For every model, a negative mold was designed and converted to stereolithography (STL) files. The STL files were 3D printed with acrylonitrile butadiene styrene material using the Stratasys Dimension Elite 3D printer (Stratasys, Rehovot, Israel) at a resolution of 178 µm. Acetone vapor was used to produce a smooth inner surface. The molds were stored in room temperature for 8-12 hours and cleaned with distilled water and dried. Polydimethylsiloxane was mixed with its curing agent and then placed into a vacuum for a total of 1 hour and 30 minutes to remove the air bubbles. Subsequently, polydimethylsiloxane was poured into the dry clean molds, which were placed in the vacuum to remove any remaining air bubbles and then put in the oven for polydimethylsiloxane curing for 48 hours at the temperature of 65° C. After curing, the silicone models were put in an acetone beaker, which was placed in an ultrasonic cleaner (Branson 1800, Cleanosonic, Virginia, USA) for 8-10 hours to dissolve all acrylonitrile butadiene styrene material.

Contrast-enhanced micro-computed tomography (µCT) imaging: All the bifurcation models were imaged with µCT (Skyscanner 1172 version 1.5) using the following parameters: image pixel size 26.94 µm, voltage 100 kV, current 100 HA, and slice thickness 27 µm. To visualize the lumen borders effectively, iodinated contrast media (37%) was injected into the lumen. The bifurcations were 3D reconstructed from the µCT images using a 3D medical imaging software (Materialise Mimics 22.0, Materialise, Leuven, Belgium) and smoothened using Meshmixer (Autodesk Research, New York, NY).

Bioreactor flow circuit for invasive imaging procedures: The silicone-based bifurcation models were placed in a custom-made flow chamber. Polyvinyl chloride tubing was connected at the inlet and outlet ports of the silicone models. A bioreactor circuit was connected to the inlet and outlet of the flow chamber, allowing circulation of 1,000 ml of deionized water at a steady flowrate of 100 ml/min at room temperature (FIG. 14, (b)). All the bifurcation models were imaged with angiography and OCT imaging of both the MV and SB.

Figure 15:
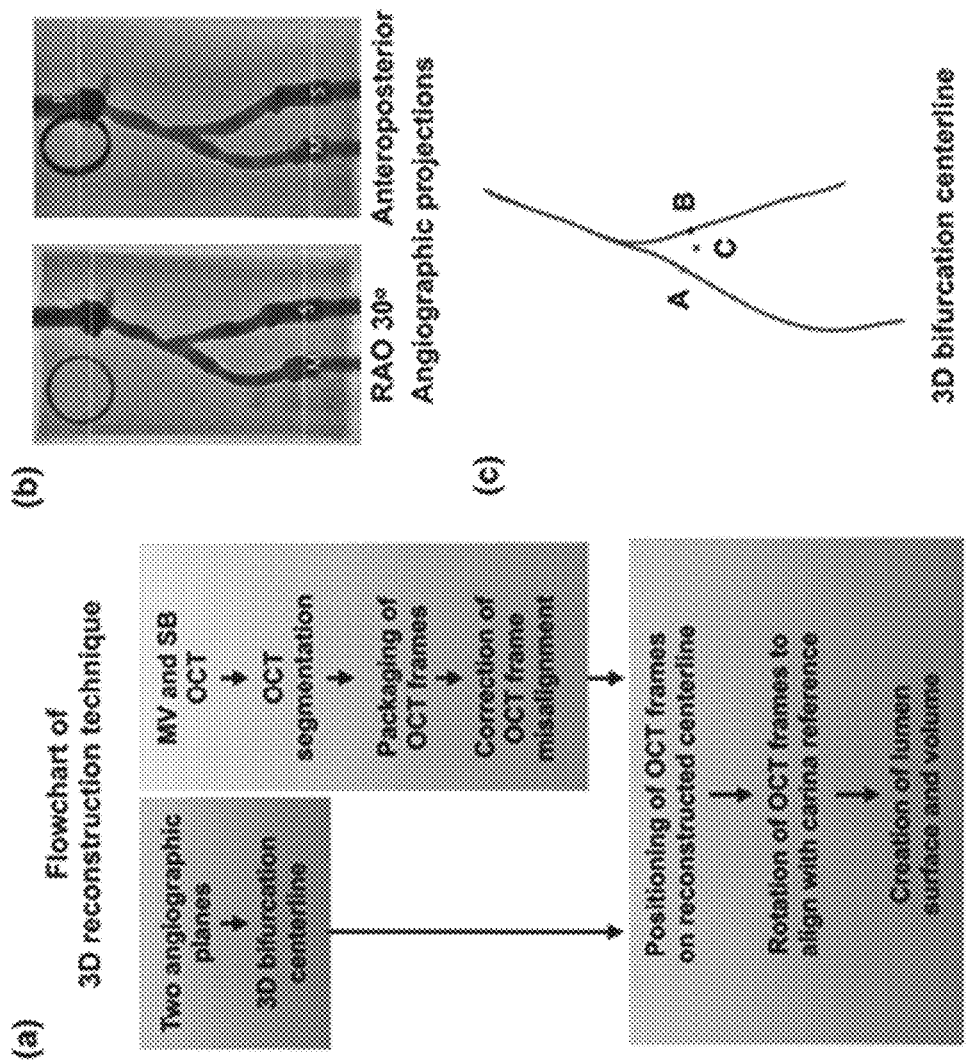
FIG. 15 illustrates a process for 3D bifurcation reconstruction steps and angiography processing, in accordance with one or more embodiments of this disclosure.

3D QCA for 3D reconstruction of bifurcation centerline: The flowchart for the 3D reconstruction of the bifurcation model is shown in FIG. 15, (a), and the detailed steps in FIGS. 15, (b) and (c) and FIG. 16. Angiography of the bifurcation models was performed at two projections with at least 30° difference in viewing angles (FIG. 16, (b)). In each projection, the lumen of the segment of interest was manually detected, and the bifurcation carina was set as a common reference location (e.g., carina reference). The 3D replica of the bifurcation models was created in CAAS and exported to VMTK (Orobix, Bergamo, Italy) for the extraction of MV and SB centerlines. On each centerline, a carina point can be found according to the carina reference projecting to the centerline (FIG. 16, (c)).

Figure 16:
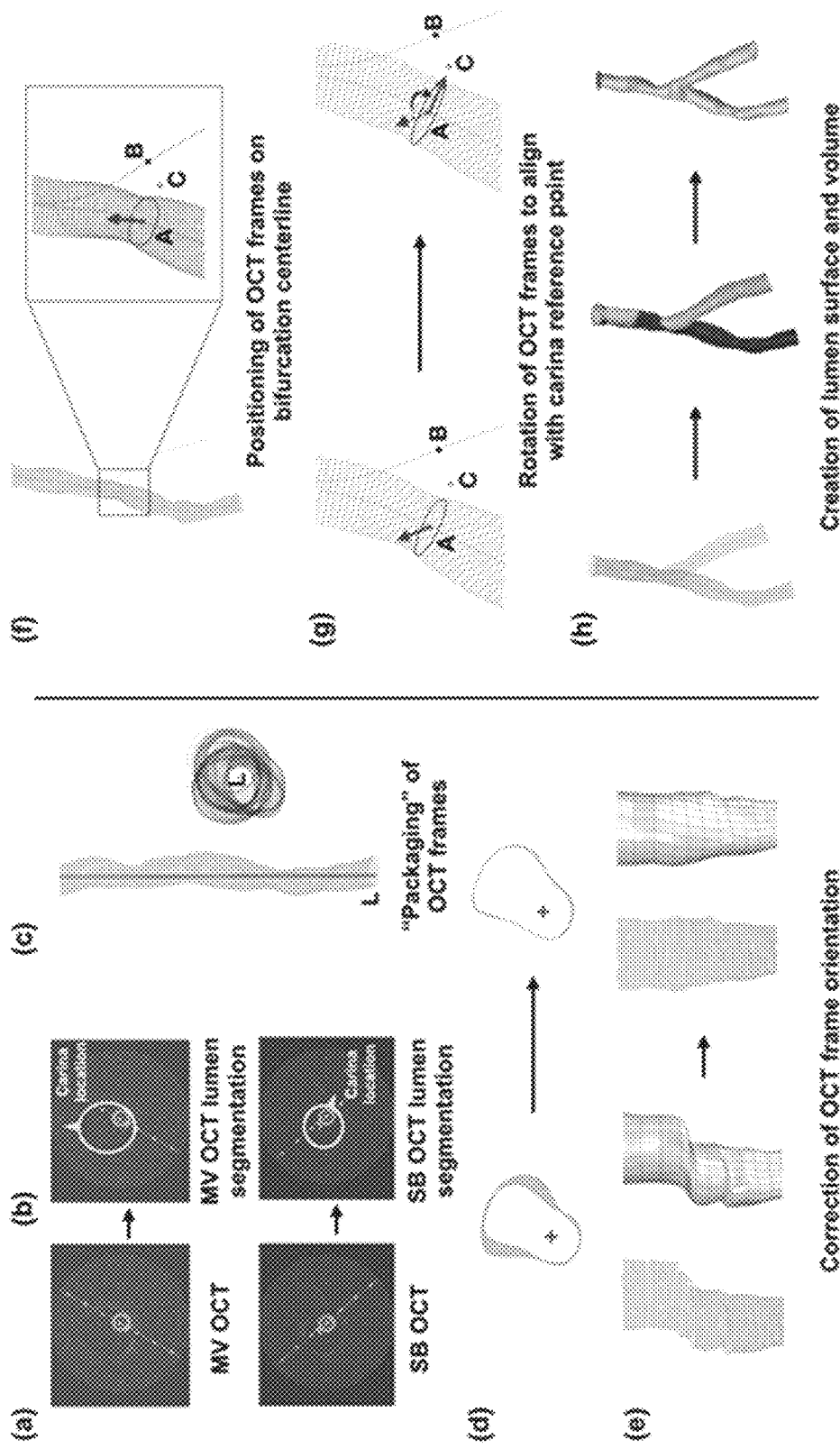
FIG. 16 illustrates a process for 3D reconstruction of bifurcation lumen from OCT, in accordance with one or more embodiments of this disclosure.

Acquisition and segmentation of OCT: OCT imaging of the MV and SB was obtained using the OPTIS Integrated System (Abbott, Chicago, IL, USA; FIG. 16, (a)). The OCT catheter (Dragonfly, Optis Imaging Catheter) was advanced through a 6F guiding catheter and pulled back (automatic triggering by saline without contrast) at a speed of 36 mm/sec (5 frames/mm) for 75 mm, covering the entire length of MV and SB from the distal to the proximal fixed marker (FIG. 14, (a)). Lumen segmentation of the OCT frames was carried out semi-automatically using echoPlaque 4.0 (INDEC Medical Systems, Los Altos, CA, USA; FIG. 16, (b)).

OCT processing for bifurcation lumen reconstruction: The detailed steps of the bifurcation lumen reconstruction are illustrated in FIG. 16. Briefly, the segmented OCT frames were imported into Grasshopper 3D (visual programming language and environment that runs within the Rhinoceros 3D) and packaged in a straight line along the catheter center (FIG. 16, (c)). The OCT frame misalignment was corrected with an in-house script (FIG. 16, (d) and (e)). The correctly aligned OCT frames were positioned perpendicularly on the respective bifurcation centerline with the centerline passing through the centroid of every frame (FIG. 16, (f)). In particular, the OCT frame at the carina was positioned at the carina point (point A in FIG. 16, (f)), and the rest of the frames were positioned in a specific location along the centerline according to the known distance between them. The frames were then rotated to align with the carina reference (point C in FIG. 16, (g)). The primary surfaces of MV and SB were created and served as a reference for the creation of a final uniform, smooth, and continuous bifurcation surface using the method of T-spline (FIG. 16, (h)).

Additional details are discussed in Wu, W. et al., "3D Reconstruction of Coronary Artery Bifurcations from Coronary Angiography and Optical Coherence Tomography:

Feasibility, Validation, and Reproducibility," Scientific Reports (2020), which is incorporated herein by reference in its entirety.

The disclosed methodology has several clinically important applications. The 3D reconstructed bifurcation can inform the proceduralists about the precise bifurcation anatomy, as well as the extent and severity of coronary artery disease. A better understanding of the disease burden can result in better procedural planning and outcomes. Moreover, the 3D reconstructed bifurcation lumen itself can be used for computational and experimental (bench) fluid dynamics studies to explore the role of flow in native coronary artery disease development and progression, as well as in-stent restenosis and thrombosis. The disclosed methodology provides the accurate geometrical input needed for realistic computational fluid dynamic studies. The disclosed technique can create the basis for finite element analysis and patient-specific computational bifurcation stenting simulations.

Furthermore, computational stenting simulations using patient-specific bifurcation anatomy and plaque properties, as well as realistic stent geometry, can provide personalized planning of stenting techniques. Patient-specific bifurcation anatomies are also particularly relevant to the industry for the testing and development of new generation stents. Finally, the basic principles of the disclosed methodology can be translated to other invasive imaging modalities, e.g., IVUS or even non-invasive imaging, e.g., coronary CTA. As long as there is imaging data available to extract the lumen centerline and lumen/vessel wall borders, the disclosed methodology has the potential to perform well.

Although the technology has been described with reference to the embodiments illustrated in the attached drawing figures, equivalents may be employed and substitutions made herein without departing from the scope of the technology as recited in the claims. Components illustrated and described herein are examples of devices and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A computational simulation platform for interventional procedures planning, comprising a computer-implemented method that includes:
   generating a mesh or meshless three-dimensional (3D) reconstruction of a vessel lumen and a surface of the vessel lumen based on invasive or non-invasive imaging;
   assigning material properties to the 3D reconstructed surface of the vessel lumen based on the invasive or non-invasive imaging, wherein the assigning of the material properties to the 3D reconstructed surface of the vessel lumen based on the invasive or non-invasive imaging includes: determining wall or plaque thickness, lumen area, plaque eccentricity and plaque constituents based on the invasive or non-invasive imaging; dividing the vessel lumen into sequential zones of plaque material; and assigning a value ranging from purely calcium plaque material to purely lipid plaque material;
   importing design and material properties of stents and balloons;
   generating a mesh or meshless model of a stent and balloon based on the imported design and material properties;
   positioning the modeled stent and balloon within the 3D reconstructed vessel lumen;
   performing balloon pre-dilation, stenting and balloon post-dilation computational simulations with the 3D reconstructed vessel lumen and surface of the vessel lumen; and
   assessing stent and vessel morphometric and biomechanical measures based on the computational simulations.

2. The computational simulation platform of claim 1, wherein the invasive or non-invasive imaging comprises at least one of: coronary angiography, intravascular ultrasound, optical coherence tomography, computed tomography angiography, or magnetic resonance angiography.

3. The computational simulation platform of claim 1, wherein the design and material properties of the stents and balloons are imported based on invasive or non-invasive imaging.

4. The computational simulation platform of claim 1, wherein the design and material properties of the stents and balloons are imported from one or more databases including manufacturer-provided data.

5. The computational simulation platform of claim 1, wherein the modeled stent and balloon in their crimped state are computationally positioned and bent in the 3D reconstructed vessel lumen.

6. The computational simulation platform of claim 1, wherein the balloon pre-dilation, stenting and balloon post-dilation computations are computationally simulated using finite element analysis.

7. The computational simulation platform of claim 1, wherein the computer-implemented method further includes:
   assigning plaque plasticity based on the material properties assigned to the 3D reconstructed surface of the vessel lumen.

8. A system for simulation and planning of interventional procedures, comprising:
   one or more medical imaging devices;
   one or more computer systems communicatively coupled to the one or more medical imaging devices, the one or more computer systems being configured to:
   generate a mesh or meshless three-dimensional (3D) reconstruction of a vessel lumen and a surface of the vessel lumen based on invasive or non-invasive imaging data received from the one or more medical imaging devices;
   assign material properties to the 3D reconstructed surface of the vessel lumen based on the invasive or non-invasive imaging data received from the one or more medical imaging devices, wherein the assigning of the material properties to the 3D reconstructed surface of the vessel lumen based on the invasive or non-invasive imaging data includes: determining wall or plaque thickness, lumen area, plaque eccentricity and plaque constituents based on the invasive or non-invasive imaging; dividing the vessel lumen into sequential zones of plaque material; and
   assigning a value ranging from purely calcium plaque material to purely lipid plaque material;
   import design and material properties of stents and balloons;
   generate a mesh or meshless model of a stent and balloon based on the imported design and material properties;

position the modeled stent and balloon within the 3D reconstructed vessel lumen;
perform balloon pre-dilation, stenting and balloon post-dilation computational simulations with the 3D reconstructed vessel lumen and surface of the vessel lumen; and
assess stent and vessel morphometric and biomechanical measures based on the computational simulations.

9. The system of claim 8, wherein the invasive or non-invasive imaging data comprise at least one of: coronary angiography data, intravascular ultrasound data, optical coherence tomography data, computed tomography angiography data, or magnetic resonance angiography data.

10. The system of claim 8, wherein the design and material properties of the stents and balloons are imported based on invasive or non-invasive imaging data received from the one or more medical imaging devices.

11. The system of claim 8, wherein the design and material properties of the stents and balloons are imported from one or more databases including manufacturer-provided data.

12. The system of claim 8, wherein the modeled stent and balloon in their crimped state are computationally positioned and bent in the 3D reconstructed vessel lumen.

13. The system of claim 8, wherein the balloon pre-dilation, stenting and balloon post-dilation computations are computationally simulated using finite element analysis.

14. The system of claim 8, wherein the one or more computer systems are further configured to:
assign plaque plasticity based on the material properties assigned to the 3D reconstructed surface of the vessel lumen.

15. A computational simulation platform for interventional procedures planning, comprising a computer-implemented method that includes:
generating a mesh or meshless three-dimensional (3D) reconstruction of a vessel lumen and a surface of the vessel lumen based on invasive or non-invasive imaging;
assigning material properties to the 3D reconstructed surface of the vessel lumen based on the invasive or non-invasive imaging, wherein the assigning of the material properties to the 3D reconstructed surface of the vessel lumen based on the invasive or non-invasive imaging includes: determining wall or plaque thickness, lumen area, plaque eccentricity and plaque constituents based on the invasive or non-invasive imaging; dividing the vessel lumen into sequential zones of plaque material; and assigning a value ranging from purely calcium plaque material to purely lipid plaque material;
performing balloon pre-dilation, stenting and balloon post-dilation computational simulations with the 3D reconstructed vessel lumen and surface of the vessel lumen; and
assessing stent and vessel morphometric and biomechanical measures based on the computational simulations.

16. The computational simulation platform of claim 15, wherein the invasive or non-invasive imaging comprises at least one of: coronary angiography, intravascular ultrasound, optical coherence tomography, computed tomography angiography, or magnetic resonance angiography.

17. The computational simulation platform of claim 15, wherein design and material properties of stents and balloons are imported based on invasive or non-invasive imaging or from one or more databases including manufacturer-provided data.

18. The computational simulation platform of claim 15, wherein modeled stent and balloon in their crimped state are computationally positioned and bent in the 3D reconstructed vessel lumen.

19. The computational simulation platform of claim 15, wherein the balloon pre-dilation, stenting and balloon post-dilation computations are computationally simulated using finite element analysis.

20. The computational simulation platform of claim 15, wherein the computer-implemented method further includes:
assigning plaque plasticity based on the material properties assigned to the 3D reconstructed surface of the vessel lumen.

* * * * *